US008039681B2

(12) United States Patent
Krusic et al.

(10) Patent No.: US 8,039,681 B2
(45) Date of Patent: Oct. 18, 2011

(54) FUNCTIONALIZED CARBON MATERIALS

(75) Inventors: Paul J. Krusic, Wilmington, DE (US);
Clarence G. Law, Newark, DE (US);
Helen S. M. Lu, Wallingford, PA (US);
Zhen-Yu Yang, Hockessin, DE (US);
Jocelyn Hicks Garner, Venice, CA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1118 days.

(21) Appl. No.: 11/205,452

(22) Filed: Aug. 17, 2005

(65) Prior Publication Data

US 2007/0293693 A1 Dec. 20, 2007

Related U.S. Application Data

(60) Provisional application No. 60/603,215, filed on Aug. 20, 2004.

(51) Int. Cl.
*C07C 22/00* (2006.01)
*C07C 19/08* (2006.01)
*H01M 8/10* (2006.01)

(52) U.S. Cl. .......................... 570/129; 429/33; 977/738

(58) Field of Classification Search .................. 429/23; 423/301, 302; 556/13, 14; 264/299
See application file for complete search history.

(56) References Cited

U.S. PATENT DOCUMENTS

| | | |
|---|---|---|
| 3,282,875 A | 11/1966 | Connolly et al. |
| 3,641,104 A | 2/1972 | Anderson et al. |
| 3,664,915 A | 5/1972 | Gore |
| 3,953,566 A | 4/1976 | Gore |
| 3,962,153 A | 6/1976 | Gore |
| 4,187,390 A | 2/1980 | Gore |
| 4,216,073 A | 8/1980 | Goldstein |
| 4,358,545 A | 11/1982 | Ezzell et al. |
| 4,940,525 A | 7/1990 | Ezzell |
| 5,277,996 A | 1/1994 | Marchetti |
| 5,300,203 A | 4/1994 | Smalley |
| 5,316,636 A | 5/1994 | Bunshah et al. |
| 5,354,926 A | 10/1994 | Fagan |
| 5,382,718 A | 1/1995 | Bekiarian |
| 5,382,719 A | 1/1995 | Fagan |
| 5,422,411 A | 6/1995 | Wei et al. |
| 5,919,583 A | 7/1999 | Grot |
| 5,922,537 A | 7/1999 | Ewart |
| 5,958,523 A | 9/1999 | Bradic |
| 5,962,746 A | 10/1999 | Diffendall et al. |
| 5,985,232 A | 11/1999 | Howard et al. |
| 6,448,412 B1 | 9/2002 | Murphy et al. |
| 6,495,290 B1 | 12/2002 | Hinokuma et al. |
| 6,645,455 B2 | 11/2003 | Margrave et al. |
| 6,706,431 B2 | 3/2004 | Kawamura |
| 6,890,676 B2 | 5/2005 | Nuber |
| 7,195,834 B2 | 3/2007 | Srinivas |
| 2002/0142206 A1 | 10/2002 | Hinokuma |
| 2003/0148161 A1 | 8/2003 | Nuber |
| 2004/0044139 A1 | 3/2004 | Grootaert |
| 2004/0057896 A1 | 3/2004 | Kronholm et al. |
| 2004/0109816 A1 | 6/2004 | Srinivas |
| 2004/0115501 A1 | 6/2004 | Hinokuma |
| 2004/0169165 A1 | 9/2004 | Srinivas |
| 2005/0009039 A1 | 1/2005 | Jagota et al. |
| 2006/0073370 A1 | 4/2006 | Krusic |
| 2006/0093885 A1 | 5/2006 | Krusic |

FOREIGN PATENT DOCUMENTS

| | | |
|---|---|---|
| EP | 1353392 | 10/2003 |
| JP | 2002063918 A | 2/2002 |
| JP | 2002216792 A | 8/2002 |
| JP | 2004014120 A | 1/2004 |
| WO | WO 92/04279 A1 | 3/1992 |
| WO | WO 00/24709 A2 | 5/2000 |
| WO | WO 00/77057 | 12/2000 |
| WO | WO 2004/112099 A2 | 12/2004 |

OTHER PUBLICATIONS

Yoshida et al., {Convenient synthesis of 1-fluoroalkyl-2-hydro[60]fullerene using fluoroalkyl halide with tributyltin hydride under radical conditions, Chemistry Letters (1996), (12), 1097-1098}.*
U.S. Appl. No. 10/716,347, filed Nov. 18, 2003, Anand Jagota et al.
H. W. Kroto et al., C60: Buckminsterfullerene, Nature, 1985, pp. 162-163, vol. 318.
Jack B. Howard et. al., Fullerenes C60 and C70 in Flames, Nature, 1991, pp. 139-141, vol. 352.
TH. Baum et. al., Fullerene Ions and Their Relation to Pah and Soot in Low-Pressure Hydrocarbon Flames, Ber. Bunsenges. Phys. Chem., 1992, pp. 841-857, vol. 96(7).
Dresselhaus et. al., C60-Related Tubules and Spherules, Sciene of Fullerness and Carbon Nanotubes, Chapter 19, 1996, p. 756-760.
Andreas Thess et. al., Crystalline Ropes of Metallic Carbon Nanotubes, Science, 1996, pp. 483-487, vol. 273.
C. Journet et. al., Large-Scale Production of Single-Walled Carbon Nanotubes by the Electric-Arc Technique, Nature, 1997, pp. 756758, vol. 388.
Pavel Nikolaev et. al., Gas-Phase Catalytic Growth of Single-Walled Carbon Nanotubes From Carbon Monoxide, Chem. Phys. Lett., 1999, pp. 91-97, vol. 313.
Jing Kong et. al., Chemical Vapor Deposition of Methane for Single-Walled Carbon Nanotubes, Chem. Phys. Lett., 1998, pp. 567-574, vol. 292.
Alan M. Cassell et. al., Large Scale CVD Synthesis of Single-Walled Carbon Nanotubes, J. Phys. Chem. B, 1999, pp. 6484-6492, vol. 103.
Yan Li et. al., Preparation of Monodispersed Fe-Mo Nanoparticles As the Catalyst for CVD Synthesis of Carbon Nanotubes, Chem. Mater., 2001, pp. 1008-1014, vol. 13.
Alan M. Cassell et. al., Directed Growth of Free-Standing Single-Walled Carbon Nanotubes, J. Am. Chem. Soc., 1999, pp. 7975-7976, vol. 121.
Ralph Krupke et. al., Separation of Metallic From Semiconducting Single-Walled Carbon Nanotubes, Science, 2003, pp. 344-347, vol. 301.

(Continued)

*Primary Examiner* — Sikarl Witherspoon

(57) ABSTRACT

This invention relates to carbon materials, such as a fullerene molecule or a curved carbon nanostructure, that are functionalized by addition chemistry performed on surface C—C double bond.

38 Claims, 1 Drawing Sheet

OTHER PUBLICATIONS

Sumio Iijima, The 60-Carbon Cluster Has Been Revealedi, J. Phys. Chem., 1987, pp. 3466-3467, vol. 91.

Hudlicky, Chemistry of Organic Fluorine Compounds, $2^{nd}$ Ed., Ellis Horwood Ltd., 1976 (Book Not Supplied).

Mohammad H. Habibi et. al.,Photochemical Addition of Perfluoro-N-Butyl Iodide to Alkynes and Olefins, J. Fluorine Chem., 1991, pp. 53-60, vol. 53.

R. N. Haszeldine et. al., Reactions of Fluorocarbon Radicals. Part VI.* The Hydration of Trifluoromethyl- and Pentafluoroethyl-Substituted Acetylenes, J. Chem. Soc., 1951, pp. 3483-3490.

Zhang Zhong et. al., Application of Pattern Recognition to Optimization of the Synthesis Process of 5-Iodine-3-Oxa Perfluoro Amyl Sulfuryl Fluoride, Hua Xue Shi Jie, 1990, p. 272-275, vol. 31(6).

G. A. Bargigia et. al., Perfluoro-W-Iodo-3-Oxaalkanesulfonyl Fluorides as Intermediates for Surfactants and Vinyl Compounds (*), J. Fluorine Chem., 1982, pp. 403-410, vol. 19.

O. Savadogo, Emerging Membranes for Electrochemical Systems Part II. High Temperature Composite Membranes for Polymer Electrolyte Fuel Cell (PEFC) Applications*, J. Power Source. 2004, pp. 135-161, vol. 127.

K. D. Kreuer, On the Development of Proton Conducting Polymer Membranes for Hydrogen and Methanol Fuel Cells, J. Membrane Sci., 2001, pp. 29-39, vol. 185.

Deborah J. Jones et. al., Recent Advances in the Functionalisation of Polybenzimidazole and Polyetherketone for Fuel Cell Applications, J. Membrane Sci., 2001, pp. 41-58, vol. 185.

Carla Heitner-Wirguin, Recent Advances in Perfluorinated Ionomer Membranes: Structure, Properties and Applications, J. Membrane Sci., 1996, pp. 1-33, vol. 120.

Satoshi Matsui et al; A Novel Reaction of [60]Fullerence, A Formal [2+2] Cycloaddition with Aryloxy- and Alkoxyketenes; *Tetrahedron Letters* 40 (1999) 899-902, Elsevier, New York.

S. Niyogi et al; Chemistry of Single-Walled Carbon Nanotubes; *Accounts of Chem. Research* 2002, 35, 1105-1113, American Chemical Society, New York.

Jeffrey L. Bahr et al; Covalent Chemistry of Single-Wall Carbon Nanotubes; *Journal of Materials Chem.*, 2002, 12, 1952-1958, The Royal Society of Chemistry, London.

Zhaoling Yao et al; Polymerization from the Surface of Single-Walled Carbon Nanotubes—Preparation and Characterization of Nanocomposites; *J. Am. Chem. Soc.*, 2003, 125, 16015-16024, American Chemical Society, New York.

Hui Hu et al; Sidewall Functionalization of Single-Walled Carbon Nanotubes by Addition of Dichlorocarbene; *J. Am. Chem. Soc.*, 2003, 125, 14893-14900, American Chemical Society, New York.

International Search Report and Written Opinion in PCT/US2005/029972, Nov. 17, 2006.

International Search Report and Written Opinion in PCT/US2005/029973, Aug. 1, 2007.

International Search Report and Written Opinion in PCT/US2005/029974, Dec. 12, 2006.

\* cited by examiner

FUNCTIONALIZED CARBON MATERIALS

The application claims the benefit of U.S. Provisional Application No. 60/603,215, filed Aug. 20, 2004, which is incorporated in its entirety as a part hereof for all purposes.

FIELD OF THE INVENTION

This invention relates to carbon materials that are functionalized by addition chemistry performed on one or more surface C—C double bonds.

BACKGROUND OF THE INVENTION

Functionalization of carbon materials is known from systems such as that described in U.S. Pat. No. 6,448,412, which discloses fullerenes substituted with a variety of different side chains to be used for biological activity. U.S. Pat. No. 6,495,290 discloses carbonaceous materials derivatized with side groups capable of transferring protons. U.S. Pat. No. 6,645,455 discloses fluorinated carbon nanotubes. Despite the availability of materials such as described above, there remains a need for carbon materials that are functionalized by addition chemistry performed with fluorinated systems on one or more surface C—C double bonds.

SUMMARY OF THE INVENTION

One embodiment of this invention is a fullerene molecule comprising n carbon atoms wherein m groups described generally by the formula

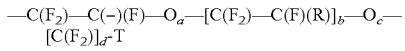

are each covalently bonded to the fullerene through formation of a 4-member ring with the unsaturated pi system of the fullerene; and wherein
  a is 0 or 1;
  b is 0 to 10;
  c is 0 or 1;
  d is 1 to 10;
  each R is independently selected from the group consisting of H, F, methyl, branched or straight-chain perfluorinated $C_1$-$C_{10}$ alkyl, phenyl and perfluorinated aryl groups;
  each T is independently selected from the group consisting of —$CO_2H$, —$SO_3H$, —$SO_2NH_2$, —$SO_2NHSO_2J$ and —$PO_3H_2$ groups;
  each J is independently selected from the group consisting of F, methyl, branched or straight-chain perfluorinated $C_1$-$C_{10}$ alkyl, phenyl and perfluorinated aryl groups;
  n is an integer from 20 to 1000; and
  m is an integer from 1 to n/2 when n is an even integer, or is an integer from 1 to (n−1)/2 when n is an odd integer.

Another embodiment of this invention is a fullerene molecule comprising n carbon atoms wherein m groups described generally by the formula

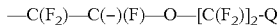

are each covalently bonded to the fullerene through formation of a 4-member ring with the unsaturated pi system of the fullerene; and wherein
  each Q is independently selected from the group consisting of —COG, —CN, —$SO_2F$ groups;
  each G is independently selected from F, Cl, $C_1$-$C_8$ alkoxy and $C_6$-$C_{12}$ aryloxy groups;
  n is an integer from 20 to 1000; and
  m is an integer from 1 to n/2 when n is an even integer, or is an integer from 1 to (n−1)/2 when n is an odd integer.

A further embodiment of this invention is a fullerene molecule comprising n carbon atoms wherein m groups described generally by the formula

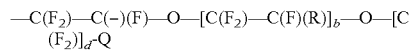

are each covalently bonded to the fullerene through formation of a 4-member ring with the unsaturated pi system of the fullerene; and wherein
  b is 1 to 10;
  d is 1 to 10;
  each R is independently selected from the group consisting of H, F, methyl, branched or straight-chain perfluorinated $C_1$-$C_{10}$ alkyl, phenyl and perfluorinated aryl groups;
  each Q is independently selected from the group consisting of —COG, —CN, —$SO_2F$ groups;
  each G is independently selected from F, Cl, $C_1$-$C_8$ alkoxy and $C_6$-$C_{12}$ aryloxy groups;
  n is an integer from 20 to 1000; and
  m is an integer from 1 to n/2 when n is an even integer, or is an integer from 1 to (n−1)/2 when n is an odd integer.

Yet another embodiment of this invention is a fullerene molecule comprising n carbon atoms wherein m groups described generally by the formula

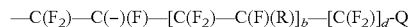

are each covalently bonded to the fullerene through formation of a 4-member ring with the unsaturated pi system of the fullerene; and wherein
  b is 0 to 10;
  d is 1 to 10;
  each R is independently selected from the group consisting of H, F, methyl, branched or straight-chain perfluorinated $C_1$-$C_{10}$ alkyl, phenyl and perfluorinated aryl groups;
  each Q is independently selected from the group consisting of —COG, —CN, —$SO_2F$ groups;
  each G is independently selected from F, Cl, $C_1$-$C_8$ alkoxy and $C_6$-$C_{12}$ aryloxy groups;
  n is an integer from 20 to 1000; and
  m is an integer from 1 to n/2 when n is an even integer, or is an integer from 1 to (n−1)/2 when n is an odd integer.

Yet another embodiment of this invention is a curved carbon nanostructure comprising carbon atoms wherein m groups described generally by the formula

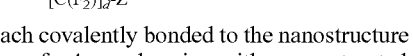

are each covalently bonded to the nanostructure through formation of a 4-member ring with an unsaturated pi system of the nanostructure; and wherein
  a is 0 or 1;
  b is 0 to 10;
  c is 0 or 1;
  d is 1 to 10;
  each R is independently selected from the group consisting of H, F, methyl, branched or straight-chain perfluorinated $C_1$-$C_{10}$ alkyl, phenyl and perfluorinated aryl groups;
  each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;
  each G is independently selected from F, Cl, $C_1$-$C_8$ alkoxy and $C_6$-$C_{12}$ aryloxy groups;
  each J is independently selected from the group consisting of F, methyl, branched or straight-chain perfluorinated $C_1$-$C_{10}$ alkyl, phenyl and perfluorinated aryl groups; and
  m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer.

Yet another embodiment of this invention is a fullerene molecule comprising n carbon atoms wherein m groups described generally by the formula

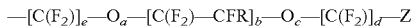

are each covalently bonded to an individual carbon atom of the fullerene; and wherein
   a is 0 or 1;
   b is 0 to 10;
   c is 0 or 1;
   d is 1 to 10;
   e is 0 to 10;
   each R is independently selected from the group consisting of H, F, methyl, branched or straight-chain perfluorinated $C_1$-$C_{10}$ alkyl, phenyl and perfluorinated aryl groups;
   each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;
   each G is independently selected from F, Cl, $C_1$-$C_8$ alkoxy and $C_6$-$C_{12}$ aryloxy groups;
   each J is independently selected from the group consisting of F, methyl, branched or straight-chain perfluorinated $C_1$-$C_{10}$ alkyl, phenyl and perfluorinated aryl groups;
   n is an integer from 20 to 1000;
   m is an integer from 1 to n/2 when n is an even integer, or is an integer from 1 to (n−1)/2 when n is an odd integer; and
   p groups selected from hydrogen and halogen are each covalently bonded to an individual carbon atom of the fullerene where p is an integer from 0 to m.

Yet another embodiment of this invention is a curved carbon nanostructure comprising carbon atoms wherein m groups described generally by the formula

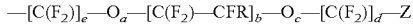

are each covalently bonded to an individual carbon atom in the nanostructure; and wherein
   a is 0 or 1;
   b is 0 to 10;
   c is 0 or 1;
   d is 1 to 10;
   e is 0 to 10;
   each R is independently selected from the group consisting of H, F, methyl, branched or straight-chain perfluorinated $C_1$-$C_{10}$ alkyl, phenyl and perfluorinated aryl groups;
   each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;
   each G is independently selected from F, Cl, $C_1$-$C_8$ alkoxy and $C_6$-$C_{12}$ aryloxy groups;
   each J is independently selected from the group consisting of F, methyl, branched or straight-chain perfluorinated $C_1$-$C_{10}$ alkyl, phenyl and perfluorinated aryl groups;
   m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer; and
   p groups selected from hydrogen and halogen are each covalently bonded to an individual carbon atom of the nanostructure where p is an integer from 0 to m.

Compositions may be formed from the fullerene molecules described above and the curved carbon nanostructures described above, or with either one or both of them and a polymer and/or a Group VIII metal

DESCRIPTION OF PREFERRED EMBODIMENTS OF THE INVENTION

Figure 1:
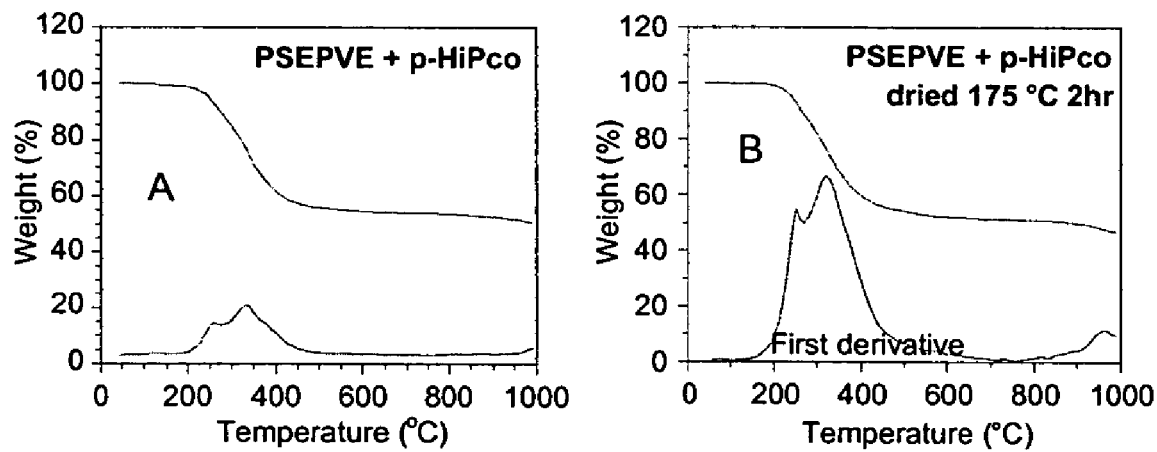
FIG. 1 is a graph of the results of thermogravimetric analysis performed on two different samples as prepared in Example 3.

In this invention, carbon materials having unsaturation are functionalized by addition chemistry performed on one or more surface C—C double bonds.

The carbon materials functionalized in this invention are those that have substantial carbon content, contain six-membered rings, exhibit curving of one or more graphitic planes (generally by including five-membered rings among the hexagons formed by the positions of the carbon atoms), and have at least one dimension on the order of nanometers. Examples of such carbon materials include, but are not limited to, a fullerene molecule and a curved carbon nanostructure. A curved carbon nanostructure includes, but is not limited to, a carbon nanotube (CNT), a fullerenic nanoparticle and carbon black, but a curved carbon nanostructure does not include a fullerene molecule.

A fullerene is a spherical allotrope of carbon, and takes the form of a closed cage molecule composed entirely of an even number of carbon atoms in the $sp^2$-hybridized state. It constitutes the third form of pure carbon, the other two being diamond and graphite. Fullerenes typically each have 12 pentagons, but differing numbers of hexagons. The most abundant species is the $C_{60}$ molecule, which is a truncated icosahedron (the highest symmetry structure possible) and has 12 pentagons and 20 hexagons. The second most abundant species of the fullerene family is $C_{70}$. The $C_{60}$ species was first reported by Kroto et al in "Carbon Vapor Produced by Laser Irradiation of Graphite, a 'Carbon Vaporization' Technique", in *Nature*, Volume 318, Pages 162-164 (1985).

Fullerenes containing up to 400 carbon atoms have also been identified including, for example, $C_{24}$, $C_{30}$, $C_{60}$, $C_{70}$, $C_{76}$, $C_{78}$, $C_{84}$, $C_{901}$, $C_{94}$, $C_{96}$ and $C_{120}$. The so-called "giant fullerenes" may be characterized as $C_{2n}$, where n is 50 or more. Giant fullerenes may be formed along with smaller fullerenes in carbon vaporization systems. For example, as reported in U.S. Pat. No. 5,985,232 (which is incorporated in its entirety as a part hereof for all purposes), carbon clusters up to $C_{632}$, all even numbered and interpreted to be fullerenes, have been observed in molecular beam mass spectrometer (MBMS) analysis of the vapor from laser vaporization of graphite. Mass spectroscopy of solvent extracts of soot from electrical vaporization of carbon rods has showed species interpreted to be $C_{188}$, $C_{208}$ and $C_{266}$. Transmission electron microscopy (TEM) of crystals consisting largely of $C_{60}$ has revealed apparently ellipsoidal fullerenes estimated to be about $C_{130}$. Scanning tunneling microscopy (STM) of extracts of soot from electrical vaporization of carbon showed spheres of 1 to 2 nm diameter, which may correspond to fullerenes up to $C_{330}$.

Fullerenes include not only single-walled but also multi-walled cages consisting of stacked or parallel layers.

Fullerenes are, in general, synthesized using a laser to ablate graphite, burning graphite in a furnace or by producing an arc across two graphite electrodes in an inert atmosphere. Other methods include negative ion/desorption chemical ionization, and combustion of a fullerene-forming fuel. Combustion is the method typically used for high volume production. In each method, condensable matter comprising a mixture of soot, other insoluble condensed matter, $C_{60}$, $C_{70}$ and higher as well as lower numbered fullerenes, and polycyclic aromatic hydrocarbons (PAH) in varying amounts is collected, with the total fullerene fraction typically between 5 and 15% of the total material collected, with the soot being 80%-95% of the remaining total material.

In other instances, fullerenes have been produced by high temperature vaporization of solid graphite rods by resistive heating or arc heating in the presence of a few to several torr of rare gas. The soot produced by the vaporization contains varying levels of fullerenes, depending on the vaporization conditions. The process described by Kroto for making fullerenes involved vaporizing the carbon from a rotating solid disk of graphite into a high-density helium flow using a focused pulsed laser. That process did not utilize a temperature controlled zone for the growth and annealing of fullerene molecules from the carbon vapor formed by the laser blast.

WO 92/04279 discloses a method for producing fullerenes involving the resistive or arc heating of graphite in the presence of an inert quenching gas to form a black soot material that contains fullerenes, predominantly $C_{60}$.

U.S. Pat. No. 5,316,636 discloses a process for producing fullerenes by electron beam evaporation of a carbon target in a vacuum. The evaporated carbon atoms or clusters are deposited onto collection substrates that are electrically charged and heated, or neutral and chilled. The resulting carbon soot is extracted to recover fullerenes. This process produces carbon soot that is rich in $C_{70}$ and higher fullerenes.

U.S. Pat. No. 5,300,203 discloses that fullerenes can be efficiently generated by vaporizing carbon with a laser beam and maintaining the vaporized carbon at conditions selected to promote fullerene growth and formation. This method of fullerene generation may be used to form new compounds including fullerenes surrounding one or more metal atoms, and fullerenes wherein one or more carbon atoms have been substituted with boron or nitrogen.

$C_{60}$ and $C_{70}$ have been successfully synthesized and collected in flames by Howard et al (Nature 352, 139-141, 1991). Evidence of high molecular weight ionic species consistent with an interpretation as being fullerenic structures was observed in low-pressure premixed benzene and acetylene flames [Baum et al, *Ber. Bunsenges. Phys. Chem.* 96, 841-857 (1992)].

Depending on molecular weight, fullerenes may soluble (for example, in toluene or xylene) and thus be solvent extractable. The procedures most commonly used for purifying fullerenes employ significant amounts of organic solvents. The solvents are used to first extract a fullerene mixture from insoluble soot and other insoluble condensed materials and then are used to purify and separate the individual fullerenes. Typically, the different constituents of the condensed matter are collected by filtration or some similar separation technique, and the soluble components are extracted by a high energy-input extraction process such as sonication or soxhlet extraction using an organic solvent such as toluene. The extraction solution is then typically filtered to eliminate the particulate matter, and then purified by high performance liquid chromatography (HPLC), which separates the fullerenes from soluble impurities, such as PAH and aliphatic species, as well as separating individual fullerene species from other fullerene species.

Fullerenes may be obtained commercially from suppliers such as Carbon Nanotechnologies Incorporated, MER Corporation, Nano-C Corporation, TDA Research Inc., Fullerene International Corp., and Luna Innovations.

A curved carbon nanostructure includes, but is not limited to, a carbon nanotube (CNT), a fullerenic nanoparticle and carbon black. The nano prefix in CNT or nanoparticle refers to dimensions in the nanometer range.

With the aid of a transition metal catalyst, carbon will assemble into single- or multiple-wall cylindrical tubes that are frequently sealed perfectly at both ends with a semi-fullerene dome, i.e. a spheroidal cap of fullerenic carbon. There may be a conical transition between the cap and the side wall. These tubes are CNTs, which may be thought of as one-dimensional single crystals of carbon. A CNT has cage-like carbon structure made up predominantly of six-member carbon rings, with minor amounts of five-member, and in some cases seven-member, carbon rings.

CNTs may have diameters ranging from about 0.6 nanometers (nm) for a single-wall carbon nanotube (SWNT) up to 3 nm, 5 nm, 10 nm, 30 nm, 60 nm or 100 nm for a SWNT or a multiple-wall carbon nanotube (MWNT). A CNT may range in length from 50 nm up to 1 millimeter (mm), 1 centimeter (cm), 3 cm, 5 cm, or greater. A CNT will typically have an aspect ratio of the elongated axis to the other dimensions greater than about 10. In general, the aspect ratio is between 10 and 2000.

A SWNT has a single shell. But in a MWNT, the inner nanotube may be surrounded by or "nested" within a number of concentric and increasingly larger tubes or particles of different diameter, and thus is known as a "nested nanotube". The MWNT may have two, five, ten, fifty or any greater number of walls (concentric CNTS). Thus, the smallest diameter tube is encapsulated by a larger diameter tube, which in turn, is encapsulated by another larger diameter nanotube, and so on.

SWNTs are much more likely to be free of defects than MWNTs because the latter have neighboring walls that provide for easily-formed defect sites via bridges between unsaturated carbon valances in adjacent tube walls. Since SWNTs have fewer defects, they are stronger and more conductive.

In defining the CNTs used in this invention, the system of nomenclature used is that which is described by Dresselhaus et al in *Science of Fullerness and Carbon Nanotubes*, chapter 19, pages 756-760 [Academic Press, San Diego, 1996 (ISBN 0-12-221820-5)]. SWNTs are distinguished from each other by a double index (n, m) where n and m are integers that describe how to cut a single strip of hexagonal "chicken-wire" graphite so that it makes the tube perfectly when it is wrapped onto the surface of a cylinder and the edges are sealed together. When the two indices are the same, m=n, the resultant tube is said to be of the "arm-chair" (or n, n) type, since when the tube is cut perpendicular to the tube axis, only the sides of the hexagons are exposed and their pattern around the periphery of the tube edge resembles the arm and seat of an arm chair repeated n times.

Most CNTs, as presently prepared, are in the form of entangled tubes. Individual tubes in the product differ in diameter, chirality and number of walls. Moreover, long tubes show a strong tendency to aggregate into "ropes" held together by Van der Waals forces. These ropes are formed due to the large surface areas of nanotubes and can contain tens to hundreds of nanotubes in one rope.

CNTs may be produced by a variety of methods, and, in addition, are available commercially. Methods of CNT synthesis include laser vaporization of graphite [Thess et al, *Science* 273, 483 (1996)], arc discharge [Journet et al, *Nature* 388, 756 (1997)], and the HiPCo (high pressure carbon monoxide) process [Nikolaev et al, *Chem. Phys. Lett.* 313, 91-97 (1999)]. Other methods for producing CNTs include chemical vapor deposition [Kong et al, *Chem. Phys. Lett.* 292, 567-574 (1998); and Cassell et al, *J. Phys. Chem.* 103, 6484-6492 (1999)]; and catalytic processes both in solution and on solid substrates [Yan Li et al, *Chem. Mater.* 13(3); 1008-1014 (2001); and A. Cassell et al, *J. Am. Chem. Soc.* 121, 7975-7976 (1999)].

As reported in U.S. Pat. No. 6,645,455, one or more transition metals of Group VIB [e.g. chromium (Cr), molybdenum (Mo), tungsten (W)] or Group VIII B transition metals [e.g. iron (Fe), cobalt (Co), nickel (Ni), ruthenium (Ru), rhodium (Rh), palladium (Pd), osmium (Os), iridium (Ir) and platinum (Pt)] catalyze the growth of CNTs and/or ropes when contacted with a carbon bearing gas such carbon monoxide and hydrocarbons, including aromatic hydrocarbons, e.g. benzene, toluene, xylene, cumene, ethylbenzene, naphthalene, phenanthrene, anthracene or mixtures thereof; non-aromic hydrocarbons, e.g. methane, ethane, propane, ethylene, propylene, acetylene or mixtures thereof; and oxygen-containing hydrocarbons, e.g. formaldehyde, acetaldehyde, acetone, methanol, ethanol or mixtures thereof. Mixtures of one or more Group VIB or VIIIB transition metals also selectively produce SWNTs and ropes of SWNTs.

A further method of making CNTs and/or ropes of CNTs involves supplying carbon vapor to the live end of one or more of CNTs growing by a catalytic process in which there is a "live end" of the nanotube in contact with a nanometer-scale transition metal particle that serves as a catalyst. The live end of the nanotube is maintained in contact with a carbon bearing feedstock gas in an annealing zone at an elevated temperature. Carbon in vapor form may be supplied by an apparatus in which a laser beam impinges on a carbon target that is maintained in a heated zone. Alternatively carbon may be added to the live end by the direct action of the catalytic particle in the annealing zone with a carbon-bearing feedstock gas such as carbon monoxide and hydrocarbons, including aromatic hydrocarbons, e.g. benzene, toluene, xylene, cumene, ethylbenzene, naphthalene, phenanthrene, anthracene or mixtures thereof; non-aromic hydrocarbons, e.g. methane, ethane, propane, ethylene, propylene, acetylene or mixtures thereof; and oxygen-containing hydrocarbons, e.g. formaldehyde, acetaldehyde, acetone, methanol, ethanol or mixtures thereof.

A particularly useful form of CNTs is that which is made by the high pressure carbon monoxide disproportionation process (these CNTs are referred to herein as "HiPCo" CNTs). These CNTs have been chemically processed to remove contaminants that include catalyst seeds. Various approaches have been taken to purify them, essentially based on one or more of the following: oxidation processes with oxidizing acids or mixtures of acids (nitric and/or sulphuric, and/or hydrochloric acid), filtration, separation by centrifugation or chromatography.

Depending on their atomic structure CNTs may have either metallic or semiconductor properties. Tubes that have C—C bonds running parallel to the circumference of the tube are in the arm-chair configuration and are metallic, and have high electrical and thermal conductivity. Tubes that have bonds running parallel to the axis of the tube are in the zig-zag configuration, and are generally semi-conducting. Additionally, there are tubes that have a helical, chiral structure and are often semi-conducting. These properties, in combination with the small dimensions of the tubes makes them particularly attractive for use in fabrication of nano-devices. The diversity of tube diameters, chiral angles and aggregation states in nanotube samples obtained from various preparation methods can, however, be a hindrance to such efforts. Aggregation is particularly problematic because the highly polarizable, smooth-sided tubes readily form parallel bundles or ropes with a large van der Waals binding energy. This bundling perturbs the electronic structure of the tubes, and hinders attempts to separate the tubes by size or type or to use them as individual macromolecular species. Because most populations of CNTs are aggregated, it is important to address this situation for the purposes of obtaining discreet populations of nanotubes that have a uniform length, diameter, chirality or other physical properties.

U.S. Ser. No. 10/716,347, which is incorporated in its entirety as a part hereof, reports a method for the facile and inexpensive separation of dispersed carbon nanotubes into populations having discreet characteristics through the use of stabilized solutions of nucleic acid molecules that have the ability to disperse and solubilize CNTs, resulting in the formation of nanotube-nucleic acid complexes. Separation of these nucleic acid associated CNTs is then performed based on common chromatographic means.

A method of separating metallic from semi-conducting SWNTs in a suspension using alternating current dielectrophoresis is reported by Krupke et al in *Science,* 301, 344-347 (2003).

Other useful forms of a curved carbon nanostructure include a fullerenic nanoparticle and carbon black. One type of fullerenic nanoparticle has a substantial amount of true fullerene character as it is curved in two dimensions. It is typically an open or closed cage carbon structure that has at least one dimension on the order of nanometers and is made up of five-member and six-member, and in some cases four-member and/or seven-member, carbon rings. Although the dimensions of the particle are often beyond those typically associated with a molecule, the atomic interactions within the nanoparticle are typically covalent in nature.

In some instances, the nanoparticle may be of approximately the same dimensions along all axes such as when it has a single shell. In other instances, the nanoparticle may be polyhedral in shape, or take the form of multiple polyhedral shells separated by about 0.34 nm (close to the interlayer spacing of graphite).

A polyhedral may be thought of as exhibiting a generally spheroidal shape although its surface is made up of smoothly continuing curved junctions between adjacent flat face. Unlike a true sphere whose surface is of approximately constant curvature and whose surface is at all points equidistant from the center, the term "spheroidal" is used to describe structures that are generally sphere-like, but are elongated along one or more axes. These spheroidal polyhedrals may have a relatively high curvature at the edges (where two faces meet) and vertices (where three faces meet).

Multishelled polyhedrons may be viewed as "nested" because an inner shell is enclosed within a polyhedral shell of larger dimension, the term "shell" referring to a curved fullerenic surface that can be ordered so as to form a nested structure. Nested spheroidal polyhedron shells of carbon have been observed in carbon deposited from an arc discharge at $10^{-7}$ torr, as reported by Iijima in *J. Phys. Chem.* 91, 3466-3467 (1987). The central shells ranged from about 1 nm diameter to much larger, some containing one- and two-layered giant fullerenes equivalent to about $C_{3700}$ and larger. Essentially spherical onion structures with up to about 70 shells have been produced by intense electron-beam irradiation of carbon soot collected from an arc-discharge apparatus. Also known, and useful as fullerenic nanoparticles, are nested spheres and polyhedral spheroids 5-20 nm in diameter and other polyhedrons of approximately triangular, tetragonal, pentagonal and hexagonal cross section.

Other types of fullerenic nanoparticles have shapes that, in large part, result from the curvature of a graphene sheet, which contains only six-member rings, and is thus curved in only one dimension. The edges of large regions of graphitic character are often but not always zipped together by the formation of five-member rings to form a shape such as a cone, a truncated cone (a "lampshade"), a prolate, trigonous or toroidal shape, or other complex shapes having both concave and convex curvature. In addition to the regions of graphitic character, these nanoparticles will often contain regions that have true fullerene character in the sense of a structure containing both six-member and five-member carbon rings. The five-member rings are often embedded where a structure becomes at least partially closed, and the five-membered rings introduce disinclination defects in the otherwise planar graphitic network.

Another form of fullerenic nanoparticles is the contents of fullerenic soot, which is typically composed of spherules of carbon made up curved graphene sheets that have substantial fullerenic character. The spherules have dimensions similar to conventional carbon black and thermal black (finely divided carbon), i.e. in the range of 5 nm to 1000 nm. Fullerenic character is noted by the presence of five-member and six-member carbon rings that result in curved sheets of carbon. Fullerenic soot is made up of spherules of curved carbon sheets that may be stacked or nested within other carbon sheets of similar geometry.

Soot is a solid particulate carbonaceous material containing primarily carbon but including hydrogen, oxygen and other elements depending on the composition of the material from which the soot is formed. Combustion-generated soot contains significant amounts of hydrogen and some oxygen, as well as trace amounts of other elements that are present in the flame. Soot produced in carbon vaporization, or other fullerene-synthesis processes, may contain smaller amounts of oxygen and hydrogen and various amounts of other elements depending on the purity of the carbon source material. The soot structure consists primarily of layers of polycyclic aromatic hydrocarbon ("PAH") that, depending on the formation conditions, may be planar or curved, and some of each shape may be present in various amounts. The layers exhibit various degrees of mutual alignment ranging from an amorphous structure early in the formation process to an increasingly crystal-like structure, either graphitic (planar layers), fullerenic (curved layers), or some of both, as residence time at high temperature increases. The soot particle is an aggregate or agglomerate of approximately spheroidal units referred to as primary particles or spherules. The number of spherules per aggregate can be as small as one or as large as 100 or more, and the shape of the aggregate can range from single-strand chains of spherules to branched chains and grape-like clusters, depending upon formation conditions. Soot may include a variety of closed-cage and open-cage nanoparticles having multiple nested or parallel layers or walls, shapes ranging from spheroidal to elongated, including onion-like nanoparticles with similar dimensions in all directions.

A fullerenic nanoparticle may be prepared by flame combustion of an unsaturated hydrocarbon fuel and oxygen in a burner chamber at sub-atmospheric pressures. The condensibles of the flame, containing the fullerenic nanoparticles, are collected as a solid or liquid at a post-flame location. The condensibles may include nanoparticles formed within the flame or during the collection process, and may include vapors which are collected as they exit the flame. Representative fuels include ethylene, indene, benzene, toluene, cresol, xylene, pyrrole, pyrroline, pyrrolidine, thiophene, pyridine, pyridizine, pyrazine, pyrimidine, indole, indoline, furan, naphthalene, indan, anthracene, pyrene, chrysene and styrene.

The fuel may be combusted in a flame at a temperature in the range of about 1700 to 2100 K. The burner chamber pressure may be in the range of about 20 to 300 torr, and is more preferably about 80 to 200 torr; diluent concentration may be in the range of 0 to about 50 vol %; and the carbon to oxygen ratio (C/O) may be in the range of about 0.85 to 1.10. Suitable diluents include argon, nitrogen, carbon dioxide, steam, flue gases and mixtures thereof.

Organic solvents, such as toluene, may be used to purify the condensed aggregation of fullerenic nanoparticles, and recover a usable product. The solvent is used to first extract the soluble from the insoluble particles, and then also to purify the individual components of the soluble fraction. The different constituents of the condensed aggregation of nanoparticles are collected by filtration or equivalent technique, and the soluble components are extracted by a high energy-input extraction process such as sonication or soxhlet extraction using an organic solvent such as toluene. The extraction solution is then typically filtered to eliminate any undesired matter, and is then purified by high performance liquid chromatography (HPLC), which separates the components from soluble impurities and separates individual components from each other. Insoluble components may be separated by size.

Methods for preparing and recovering a fullerenic nanoparticle are further described in U.S. Pat. No. 5,985,232 and US 2004/057,896, each of which is incorporated in its entirety as a part hereof. Fullerenic nanoparticles are available commercially from suppliers such as Nano-C Corporation, Westwood Mass.

Carbon black is a powdered form of highly dispersed, amorphous elemental carbon. It is a finely divided, colloidal material in the form of spheres and their fused aggregates. Types of carbon black are characterized by the size distribution of the primary particles, and the degree of their aggregation and agglomeration. Average primary particle diameters range from 10 to 400 nm, while average aggregate diameters range from 100 to 800 nm. Carbon black is often popularly, but incorrectly, regarded as a form of soot. Carbon black is manufactured under controlled conditions whereas soot is randomly formed, and they can be distinguished on the basis of tar, ash content and impurities. Carbon black is made by the controlled vapor-phase pyrolysis and/or thermal cracking of hydrocarbon mixtures such as heavy petroleum distillates and residual oils, coal-tar products, natural gas and acetylene. Acetylene black is the type of carbon black derived from the burning of acetylene. Channel black is made by impinging gas flames against steel plates or channel irons (from which the name is derived), from which the deposit is scraped at intervals. Furnace black is the term sometimes applied to carbon black made in a refractory-lined furnace. Lamp black, the properties of which are markedly different from other carbon blacks, is made by burning heavy oils or other carbonaceous materials in closed systems equipped with settling chambers for collecting the solids. Thermal black is produced by passing natural gas through a heated brick checkerwork where it thermally cracks to form a relatively coarse carbon black. Over 90% of all carbon black produced today is furnace black. Carbon black is available commercially from numerous suppliers such as Cabot Corporation.

In this invention, functionalization is achieved by addition chemistry performed on one or more surface C—C double bonds of a carbon nanostructure. One suitable method for performing an addition reaction is a cycloaddition reaction such as that of fluoroalkenes with themselves and other alkenes to form fluorocyclobutane rings. This is referred to herein as a "2+2" addition. Another suitable method is the addition of fluorinated radicals to the C—C double bond.

These types of processes are described by Hudlicky in *Chemistry of Organic Fluorine Compounds*, 2nd ed, Ellis Horwood Ltd., 1976.

In one embodiment of this invention, such a cycloaddition process may be performed in a reaction brought about by heating a fullerene molecule with a compound described generally by the formula $$CF_2=CF-O_a-[C(F_2)-C(F)(R)]_b-O_c-[C(F_2)]_d-T \qquad I$$

wherein
a is 0 or 1;
b is 0 to 10;
c is 0 or 1;
d is 1 to 10;
each R is independently selected from the group consisting of H, F, methyl, branched or straight-chain perfluorinated $C_1$-$C_{10}$ alkyl, phenyl and perfluorinated aryl groups;
each T is independently selected from the group consisting of —$CO_2H$, —$SO_3H$, —$SO_2NH_2$, —$SO_2NHSO_2J$ and —$PO_3H_2$ groups; and
each J is independently selected from the group consisting of F, methyl, branched or straight-chain perfluorinated $C_1$-$C_{10}$ alkyl, phenyl and perfluorinated aryl groups. The compounds described in Formula I may be prepared in the manner set forth in U.S. Pat. Nos. 3,282,875 and 3,641,104.

The above reaction will produce a fullerene molecule comprising n carbon atoms wherein m functional branches described generally by the formula $$-C(F_2)-C(-)(F)-O_a-[C(F_2)-C(F)(R)]_b-O_c-[C(F_2)]_d-T \qquad II$$

are each covalently bonded to the fullerene through formation of a 4-member ring with the unsaturated pi system of the fullerene, and a, b, c, d, R and T are as set forth above.

The bonds resulting from opening a C=C bond in both the fullerene and a compound of Formula I, the ensuing 2+2 cycloaddition, create the 4-member ring. As the ring itself is not shown in Formula II, its presence is indicated by the incomplete bonds of the —$C(F_2)$ and $C(-)$ residues shown therein. This same graphical representation of a 4-membered ring is also used in Formulae IV, VI, VIII and X.

In other alternative embodiments:
a and b may both be 0, c may be 0 or 1 (preferably 1), and d may be 1 to 4 or 1 to 2;
a may be 1, c may be 1, and b and/or d may be 1 to 4 or 1 to 2;
a, b and c may all be 0, and d may be 1 to 4 or 1 to 2;
a may be 0, c may be 1, b may be 1 to 4 or 1 to 2, and d may be 2 to 4;
when a and b are both 0, c may be 0 or 1 (preferably 1), d may be 1 to 4 or 1 to 2, T may be selected from the group consisting of —$SO_3H$, —$SO_2NH_2$, —$SO_2NHSO_2J$ and —$PO_3H_2$ groups, and J may be F or $CF_3$ groups;
when a is 1 and c is 1, b and/or d may be 1 to 4 or 1 to 2, R may be $CF_3$, T may be selected from the group consisting of —$SO_3H$, —$SO_2NH_2$, —$SO_2NHSO_2J$ and —$PO_3H_2$ groups, and J may be F or $CF_3$ groups;
when a, b and c are all 0, d may be 1 to 4 or 1 to 2, T may be selected from the group consisting of —$SO_3H$, —$SO_2NH_2$, —$SO_2NHSO_2J$ and —$PO_3H_2$ groups, and J may be F or $CF_3$ groups; and/or
when a is 0 and c is 1, b may be 1 to 4 or 1 to 2, R may be $CF_3$, d may be 2 to 4, T may be selected from the group consisting of —$SO_3H$, —$SO_2NH_2$, —$SO_2NHSO_2J$ and —$PO_3H_2$ groups, and J may be F or $CF_3$ groups.

In another embodiment of this invention, a cycloaddition process may be performed in a reaction brought about by heating a fullerene molecule with a compound described generally by the formula $$CF_2=CF-O-[C(F_2)]_2-Q \qquad III$$

wherein
each Q is independently selected from the group consisting of —COG, —CN, —$PO_3H_2$, and —$SO_2F$ groups; and
each G is independently selected from F, Cl, $C_1$-$C_8$ alkoxyl and $C_6$-$C_{12}$ aryloxy groups. The compounds described by Formula III may be prepared in the manner set forth in U.S. Pat. No. 4,358,545.

The above reaction will produce a fullerene molecule comprising n carbon atoms wherein m functional branches described generally by the formula $$-C(F_2)-C(-)(F)-O-[C(F_2)]_2-Q \qquad IV$$

are each covalently bonded to the fullerene through formation of a 4-member ring with the unsaturated pi system of the fullerene, and Q is as set forth above.

In other alternative embodiments, Q may be a —$SO_2F$ group.

In a further embodiment of this invention, a cycloaddition process may be performed in a reaction brought about by heating a fullerene molecule with a compound described generally by the formula $$CF_2=CF-O-[C(F_2)-C(F)(R)]_b-O-[C(F_2)]_d-Q \qquad V$$

wherein
b is 1 to 10;
d is 1 to 10;
each R is independently selected from the group consisting of H, F, methyl, branched or straight-chain perfluorinated $C_1$-$C_{10}$ alkyl, phenyl and perfluorinated aryl groups; and
each Q is independently selected from the group consisting of —COG, —CN, —$PO_3H_2$, and —$SO_2F$ groups; and
each G is independently selected from F, Cl, $C_1$-$C_8$ alkoxyl and $C_6$-$C_{12}$ aryloxy groups. The compounds described in Formula V may be prepared in the manner set forth in U.S. Pat. Nos. 3,282,875 and 3,641,104.

The above reaction will produce a fullerene molecule comprising n carbon atoms wherein m functional branches described generally by the formula $$-C(F_2)-C(-)(F)-O-[C(F_2)-C(F)(R)]_b-O-[C(F_2)]_d-Q \qquad VI$$

are each covalently bonded to the fullerene through formation of a 4-member ring with the unsaturated pi system of the fullerene, and b, d, R and Q are as set forth above In other alternative embodiments, b and/or d may be 1 to 4 or 1 to 2, R may be a $CF_3$ group, and/or Q may be a —$SO_2F$ group.

In yet another embodiment of this invention, a cycloaddition process may be performed in a reaction brought about by heating a fullerene molecule with a compound described generally by the formula $$CF_2=CF-[C(F_2)-C(F)(R)]_b-[C(F_2)]_d-Q \qquad VII$$

wherein
b is 0 to 10;
d is 1 to 10;
each R is independently selected from the group consisting of H, F, methyl, branched or straight-chain perfluorinated $C_1$-$C_{10}$ alkyl, phenyl and perfluorinated aryl groups; and
each Q is independently selected from the group consisting of —COG, —CN, —$PO_3H_2$, and —$SO_2F$ groups; and each G is independently selected from F, Cl, $C_1$-$C_8$ alkoxyl and $C_6$-$C_{12}$ aryloxy groups. The compounds described in Formula VII may be prepared in the manner set forth in WO 00/24709.

The above reaction will produce a fullerene molecule comprising n carbon atoms wherein m functional branches described generally by the formula $$—C(F_2)—C(-)(F)—[C(F_2)—C(F)(R)]_b—[C(F_2)]_d-Q \quad \text{VIII}$$

are each covalently bonded to the fullerene through formation of a 4-member ring with the unsaturated pi system of the fullerene; and b, d, R and Q are as set forth above.

In other alternative embodiments, b and/or d may be 1 to 4 or 1 to 2, R may be a $CF_3$ group, and/or Q may be a —$SO_2F$ group.

In yet another embodiment of this invention, a cycloaddition process may be performed in a reaction brought about by heating a curved carbon nanostructure with a compound of the formula $$CF_2=CF—O_a—[C(F_2)—C(F)(R)]_b—O_c—[C(F_2)]_d—Z \quad \text{IX}$$

wherein
a is 0 or 1;
b is 0 to 10;
c is 0 or 1;
d is 1 to 10;
each R is independently selected from the group consisting of H, F, methyl, branched or straight-chain perfluorinated $C_1$-$C_{10}$ alkyl, phenyl and perfluorinated aryl groups;
each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups; and
each J is independently selected from the group consisting of F, methyl, branched or straight-chain perfluorinated $C_1$-$C_{10}$ alkyl, phenyl and perfluorinated aryl groups; and
each G is independently selected from F, Cl, $C_1$-$C_8$ alkoxyl and $C_6$-$C_{12}$ aryloxy groups. The compounds described in Formula IX may be prepared in the manner set forth in U.S. Pat. No. 3,282,875 and U.S. Pat. No. 3,641,104.

The above reaction will produce a curved carbon nanostructure comprising m carbon atoms having functional branches described generally by the formula $$—C(F_2)—C(-)(F)—O_a—[C(F_2)—C(F)(R)]_b—O_c—[C(F_2)]_d—Z \quad \text{X}$$

wherein each functional branch is covalently bonded to the curved carbon nanostructure through formation of a 4-member ring with an unsaturated pi system of the compound; and wherein a, b, c, d, R and Z are as set forth above.

In other alternative embodiments:
a and b may both be 0, c may be 0 or 1 (preferably 1), and d may be 1 to 4 or 1 to 2;
a may be 1, c may be 1, and b and/or d may be 1 to 4 or 1 to 2;
a, b and c may all be 0, and d may be 1 to 4 or 1 to 2;
a may be 0, c may be 1, b may be 1 to 4 or 1 to 2, and d may be 2 to 4;
when a and b are both 0, c may be 0 or 1 (preferably 1), d may be 1 to 4 or 1 to 2, Z may be selected from the group consisting of —$SO_3H$, —$SO_2NH_2$, —$SO_2NHSO_2J$ and —$PO_3H_2$ groups, and J may be F or $CF_3$ groups;
when a is 1 and c is 1, b and/or d may be 1 to 4 or 1 to 2, R may be $CF_3$, Z may be selected from the group consisting of —$SO_3H$, —$SO_2NH_2$, —$SO_2NHSO_2J$ and —$PO_3H_2$ groups, and J may be F or $CF_3$ groups;

when a, b and c are all 0, d may be 1 to 4 or 1 to 2, Z may be selected from the group consisting of —$SO_3H$, —$SO_2NH_2$, —$SO_2NHSO_2J$ and —$PO_3H_2$ groups, and J may be F or $CF_3$ groups; and/or
when a is 0 and c is 1, b may be 1 to 4 or 1 to 2, R may be $CF_3$, d may be 2 to 4, Z may be selected from the group consisting of —$SO_3H$, —$SO_2NH_2$, —$SO_2NHSO_2J$ and —$PO_3H_2$ groups, and J may be F or $CF_3$ groups.

Any of the processes mentioned above may be run by heating a fullerene molecule with one of the compounds as described, respectively, in Formulae I, III, V, or VII; or by heating a curved carbon nanostructure with a compound as described in Formula IX. The process is run at a temperature in the range of about 100° C. to about 350° C., preferably in the range of about 150° C. to about 300° C., and more preferably in the range of about 200° C. to about 300° C. The reaction may be run without solvent, or with an organic or halocarbon solvent (such as 1,2,4-trichlorobenzene), under an autogenous pressure of the Formulae I, III, V, VII or IX compound, for a period of time in the range of about 1 hour to about 96 hours, and preferably in the range of about 1 hour to about 18 hours. Typically the reaction is carried out in a sealed, stainless steel pressure vessel, with a pressure gauge for determining the pressure, and an internal thermocouple for measuring temperature.

The product from any of the above reactions is generally isolated by first evaporating, distilling off under reduced pressure, or filtering out all, or most of, any excess of the Formulae I, III, V, VII or IX compound and any solvent (if used). In the case where the product is insoluble, the product may be collected by filtration, and washed with organic or haloorganic solvents such as tetrahydrofuran, methylene chloride, acetone, 1,1,2-trichlorotrifluoroethane or hexafluorobenzene. The product is heated under reduced pressure to remove residual solvent and/or reagents. Alternatively, the product is re-dissolved (or dissolved) in an organic or halocarbon solvent such as tetrahydrofuran, 1,1,2-trichlorotrifluoroethane or hexafluorobenzene, and is then filtered. The solvent is then evaporated under reduced pressure. If the product is soluble, addition of an organic or haloorganic solvent such as hexane allows for collection of the product by filtration, or cooling to –78° C. will precipitate the product in a form in which it can be then be collected. The result is a functionalized fullerene molecule to which has been bonded through a 4-member ring, as a residue of the starting compound, a functional branch as shown respectively in Formulae II, IV, VI and VIII; or a functionalized curved carbon nanostructure to which has been bonded through a 4-member ring, as a residue of the starting compound, a functional branch as shown in Formula X.

Other suitable processes for performing an addition reaction on a carbon nanostructure include (1) a photolysis process such as is known for the preparation of fluoroalkylated organic compounds, and is described, for example, by Habibi et al in *J. Fluorine Chem.*, Volume 53, Pages 53-60 (1991); and (2) a thermolysis process such as is known for the preparation of fluoroalkylated organic compounds, and is described, for example, by Haszeldine et al in *J. Chem. Soc.*, page 3483 (1952).

In one embodiment of this invention, such a photolysis or thermolysis process may be performed by reacting a fullerene molecule or a curved carbon nanostructure with a compound described generally by the formula $$X—[C(F_2)]_e—O_a—[C(F_2)—CFR]_b—O_c—[C(F_2)]_d—Z \quad \text{XI}$$

or by the formula

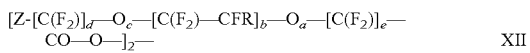

wherein
  a is 0 or 1;
  b is 0 to 10;
  c is 0 or 1;
  d is 1 to 10;
  e is 1 to 10;
  each R is independently selected from the group consisting of H, F, methyl, branched or straight-chain perfluorinated $C_1$-$C_{10}$ alkyl, phenyl and perfluorinated aryl groups;
  each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;
  each G is independently selected from the group consisting of F, Cl, $C_1$-$C_8$ alkoxy and $C_6$-$C_{12}$ aryloxy groups;
  each J is independently selected from the group consisting of F, methyl, branched or straight-chain perfluorinated $C_1$-$C_{10}$ alkyl, phenyl and perfluorinated aryl groups; and
  each X is independently selected from Br and I groups.

The compounds described by Formula XI may be prepared in the manner set forth in Zhang et al in *Huaxue Shijie,* 1990, 31, 272; and (b) Bargigia et al in *J. Fluorine Chem.,* 1982, 19, 403. The compounds described by Formula XII may be prepared in the manner set forth in U.S. Pat. No. 5,962,746.

The above reaction will produce a fullerene molecule comprising n carbon atoms wherein m groups described generally by the formula

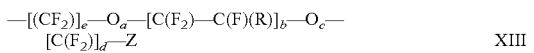

are each covalently bonded to a carbon atom in the fullerene; and wherein a, b, c, d, e, R and Z are as set forth above.

The above reaction will also produce a curved carbon nanostructure comprising m carbon atoms having functional branches described generally by the formula

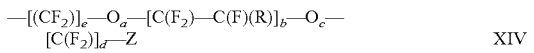

wherein each functional branch is covalently bonded to a carbon atom in the curved carbon nanostructure; and wherein a, b, c, d, e, R and Z are as set forth above.

In other alternative embodiments of either the fullerene molecule containing a functional branch of Formula XIII, or the curved carbon nanostructure containing a functional branch of Formula XIV:
  a and b may both be 0, c may be 0 or 1 (preferably 1), and d and/or e may be 1 to 4 or 1 to 2;
  a may be 1, c may be 1, and b, d and/or e may be 1 to 4 or 1 to 2;
  a, b and c may all be 0, and d and/or e may be 1 to 4 or 1 to 2;
  a may be 0, c may be 1, b and/or e may be 1 to 4 or 1 to 2, and d may be 2 to 4;
  when a and b are both 0, c may be 0 or 1 (preferably 1), d and/or e may be 1 to 4 or 1 to 2, Z may be selected from the group consisting of —$SO_3H$, —$SO_2NH_2$, —$SO_2NHSO_2J$ and —$PO_3H_2$ groups, and J may be F or $CF_3$ groups;
  when a is 1 and c is 1, b, d and/or e may be 1 to 4 or 1 to 2, R may be $CF_3$, Z may be selected from the group consisting of —$SO_3H$, —$SO_2NH_2$, —$SO_2NHSO_2J$ and —$PO_3H_2$ groups, and J may be F or $CF_3$ groups;
  when a, b and c are all 0, d and/or e may be 1 to 4 or 1 to 2, Z may be selected from the group consisting of —$SO_3H$, —$SO_2NH_2$, —$SO_2NHSO_2J$ and —$PO_3H_2$ groups, and J may be F or $CF_3$ groups; and/or
  when a is 0 and c is 1, b and/or e may be 1 to 4 or 1 to 2, R may be $CF_3$, d may be 2 to 4, T may be selected from the group consisting of —$SO_3H$, —$SO_2NH_2$, —$SO_2NHSO_2J$ and —$PO_3H_2$ groups, and J may be F or $CF_3$ groups.

Utilizing a photolysis alkylation process to prepare a functionalized fullerene molecule or curved carbon nanostructure in accordance with this invention involves photolysing with a mercury lamp or other source of ultraviolet and visible light a solution or slurry of fullerene molecule or curved carbon nanostructure with a compound of Formula XI or XII with or without an organic or halocarbon solvent for a period in the range of about 10 minutes to about 48 hours, usually about 10 minutes to about two hours, and under an inert gas atmosphere such as dinitrogen in the absence of oxygen. Examples of suitable organic or halocarbon solvents include hexafluorobenzene, 1,2,4-trichlorobenzene, Freon™ 113 fluorocarbon from DuPont.

Utilizing a thermal fluoroalkylation process to prepare a functionalized fullerene molecule or curved carbon nanostructure in accordance with this invention involves heating a fullerene molecule or a curved carbon nanostructure with a compound of Formula XI at a temperature in the range of about 160° C. to about 350° C., and preferably in the range of about 180° C. to about 300° C. The reaction may be run with or without an organic or halocarbon solvent, such as 1,2,4-trichlorobenzene or hexafluorobenzene, under an autogenous pressure for a period in the range of about 1 hour to about 96 hours, preferably in the range of about 1 hour to about 48 hours. Typically the reaction is carried out in a glass Fisher-Porter bottle equipped with a pressure gauge, internal thermocouple for measuring temperature, and nitrogen gas inlet for pressurizing the apparatus.

Alternatively, the fullerene molecule or the curved carbon nanostructure may be reacted with a compound of Formula XII at a temperature in the range of about 25° C. to about 100° C. in a halocarbon solvent (such as Freon™ 113 fluorocarbon from DuPont) under an inert gas atmosphere (such as nitrogen) at an autogenous pressure for a period in the range of about 1 hour to about 96 hours.

The product from the above reactions is generally isolated by first distilling off under reduced pressure, or filtering off, all or most of any excess of the Formulae XI or XII compound, halogen and any solvent used. In the case of soluble product, product is dissolved in a halocarbon such as Freon™ 113 fluorocarbon from DuPont, $CClF_2CCl_2F$, or hexafluorobenzene and filtered. An organic or halocarbon solvent in which the product is not soluble is added to the filtrate, and the product is isolated by decantation of the supernatant, or collecting the product by filtration, after which it is dried. Alternatively, the halocarbon may be removed under reduced pressure to yield the product, which is washed with an organic solvent and then dried. In the case of insoluble product, the product is collected by filtration, and washed with organic or halocarbon solvents such as methylene chloride, acetone, Freon™ 113 fluorocarbon from DuPont, $CClF_2CCl_2F$, or hexafluorobenzene. The resulting product is heated under reduced pressure to remove residual solvents or reagents.

In the case of a fullerene molecule having a functional branch as described, respectively, in Formulae II, IV, VI, VIII or XIII,
  each n is independently an integer from about 20 to 1000;
  each m is independently an integer from about 1 to n/2 when n is an even integer, or is an integer from about 1 to (n−1)/2 when n is an odd integer; and p groups selected from hydrogen and halogen may each also be covalently bonded to an individual carbon atom of the fullerene molecule where p is an integer from 0 to m.

In other alternative embodiments, each n may independently be 60 to 100, such as 60, 70 or 84, or mixtures of any two or more thereof.

In the case of a curved carbon nanostructure having a functional branch as described, respectively, in Formulae X or XIV, m is an integer from 1 to half of the number of carbon atoms in the nanostructure in the case where the number of carbon atoms in the nanostructure is an even integer; or m is an integer from 1 to half minus 0.5 of the number of carbon atoms in the nanostructure when the number of carbon atoms in the nanostructure is an odd integer; and p groups selected from hydrogen and halogen may each also be covalently bonded to an individual carbon atom of the nanostructure where p is an integer from 0 to m.

In the case of either
(a) a compound as described, respectively, in Formulae III, V, VII or XI to be reacted with a fullerene molecule,
(b) a fullerene molecule having a functional branch as described, respectively in Formulae IV, VI, VIII or XIII,
(c) a compound as described, respectively, in Formulae IX or XII to be reacted with a curved carbon nanostructure, or
(d) a curved carbon nanostructure having a functional branch as described, respectively, in Formulae X or XIV, a terminal —$SO_2F$ group may be hydrolyzed to prepare a —$SO_3M$ group, where M is an alkali cation, by treatment with a base such as the hydroxide or carbonate of an alkali metal such as Li, Na, K or Cs in an aqueous alcohol such as methyl or ethyl alcohol. A terminal —$SO_2F$ group can also be converted to the sulfonic acid group —$SO_3H$ by treatment with a base, as above, followed by acidification. If the —$SO_3M$ functionalized material is not soluble in water, as may be the case for functionalized curved carbon nanostructures, acid treatment alone is effective, followed by filtration and washing. If the —$SO_3M$ functionalized material is soluble in water, as may be the case for functionalized fullerene materials, passage through an ion exchange column is appropriate to exchange the alkali cation with the H cation.

In the case of either a fullerene molecule having a functional branch as described, respectively in Formulae II, IV, VI, VIII or XIII, or in the case of a curved carbon nanostructure having a functional branch as described, respectively, in Formulae X or XIV, T may alternatively be selected from the group consisting of —$SO_3H$, —$SO_2NH_2$, —$SO_2NHSO_2J$ and —$PO_3H_2$ groups; J may alternatively be selected from F or $CF_3$; and the term aryl refers to monocyclic, bicyclic or tricyclic aromatic groups containing from 6 to 14 carbons in the ring portion, such as phenyl, naphthyl, substituted phenyl, or substituted naphthyl, wherein the substituent on either the phenyl or naphthyl ring may be for example $C_{1-4}$ alkyl, halogen or $C_{1-4}$ alkoxy. Moreover, the term alkoxy refers to the residue of an alkyl alcohol bonded through the oxygen atom. The term alkyl refers to both straight and branched chain radicals, for example methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the various branched chain isomers thereof. The chain may be linear or cyclic, saturated or unsaturated, containing, for example, double and triple bonds. The alkyl chain may be interrupted or substituted with, for example, one or more halogen, oxygen, silyl or other substituents. The term aryloxy refers to the residue of an aryl alcohol bonded through the oxygen atom.

Another aspect of this invention is the formation of compositions by the admixture of the functionalized fullerene molecules and the functionalized curved carbon nanostructures, as described above, with (i) each other, (ii) one or more catalytic metals such as Group VIII metals (Ru, Rh, Pd, Os, Ir and/or Pt), particularly Pt and/or Ru; and/or (iii) one or more polymers, including copolymers, that may have varying degrees of fluorination. Where it is desired to prepare a composition containing a Group VIII metal and a functionalized carbon material of this invention, it may also be desired to impregnate the carbon material with the Group VIII metal before reacting a functional group precursor with the carbon material to achieve functionalization.

In general, any film-forming polymer is suitable for use in a composition of this invention. Preferred polymers are those that can withstand high temperatures and/or harsh chemical environments, that are substantially or completely fluorinated, and/or that have ionic functionality (an "ionomer"). Useful ionic functionality includes the presence of a cation exchange group that is capable of transporting protons, such as a sulfonate, carboxylate, phosphonate, imide, sulfonimide or sulfonamide group.

The polymer used to form a composition of this invention may be non-fluorinated, substantially fluorinated or perfluorinated. A substantially fluorinated polymer is one that has fluorine substituted for hydrogen in at least 60 percent of the C—H bonds.

Examples of various polymers suitable for use in a composition of this invention are one or more of the following
polyethylene,
polypropylene,
poly(phenylene ether),
poly(phenylene sulfide),
aromatic polysulfone,
aromatic polyimide or polyetherimide
polybenzimidazole; or
a polymer prepared from one or more of the following monomers
    a fluorinated vinyl or vinylidine monomer such as include tetrafluoroethylene, hexafluoropropylene, vinyl fluoride, vinylidine fluoride, trifluorethylene, chlorotrifluoroethylene, perfluoro(alkyl vinyl ether), and mixtures thereof;
    a fluorinated styrene such as sulfonated α, β, β-trifluorostyrene or p-sulfonyl fluoride-α, β, α-trifluorostyrene (as described, for example, in U.S. Pat. No. 5,422,411);
    a sulfonated aryl ether (ether) ketone, where suitable sulfonation is obtained from the presence of a sulfonic acid group or an alkali metal or ammonium salt of a sulfonic acid group; or
    a vinyl fluoro sulfonic acid, or an analog thereof, such as a sulfonyl fluoride.

Examples of a suitable vinyl fluoro sulfonic acid or analog include and $CF_2$=$CFR^2$—$SO_3H$, where $R^2$ is selected from the group consisting of H, F, and branched or straight-chain perfluorinated $C_1$-$C_{10}$ alkyl, phenyl and perfluorinated aryl; $CF_2$=CF—O—[$C(F_2)$]$_2$—$SO_2F$; and $CF_2$=CF—O—$CF_2$—[$CF(CF_3)$]—O—[$C(F_2)$]$_2$—$SO_2F$.

When a copolymer is desired, it may be formed using a comonomer such as a vinyl or ethylenic compound that is substituted, such as tetrafluorethylene, or has ionic or other functionality.

Polymers as named above, or polymers made from one or more of the above named monomers, may be made by methods known in the art. For example, tetrafluoroethylene can be polymerized in an aqueous medium using little or no dispersing agent and vigorous agitation. Vinylidine fluoride can be polymerized in an aqueous suspension with the aid of an oil-soluble free radical initiator in the presence of a suspending agent and a chain regulator. Poly(phenylene ether) can be made by the oxidative coupling of phenol monomers, such as 2,6-dimethylphenol, using a catalyst such as a copper halide salt and pyridine. Poly(phenylene sulfide) can be made from p-dichlorobenzene and sodium sulfide in a dipolar aprotic solvent. An aromatic polysulfone can be made from 4,4'-dichlorophenylsulfone and a bisphenol in an aprotic solvent at 130-160° C. An aromatic polyimide can be made from an aromatic diamine such as phenylenediamine and an aromatic dianhydride such as pyromellitic dianhydride in a dipolar aprotic solvent. An aromatic polyetherimide can be prepared from a bisphenoxide salt and an aromatic dinitrobisimide. Styrenes may be polymerized by free radical addition using an initiator such as a peroxide. A poly(ether ketone) may be either ether rich or ketone rich, and may be prepared by polymerization of cyclic ester ketone compounds in solution or mass promoted by an initiator, or in solution with a Lewis acid by the reaction of terephthaloyl chloride with 4,4'-diphenoxybenzophenone, or the polycondensation of p-phenoxybenzoyl chloride with itself. A vinyl fluoro sulfonic acid or analog may be polymerized in a liquid medium at moderate heat using an initiator such as an azo initiator.

Other polymers suitable for use in a composition of this invention, and other methods for making such a polymer, are described in sources such as: Savadogo, *J. Power Source,* 2004, 127, 135; Kreuer, J. *Membrane Sci.,* 2001, 185, 29; Jones et al, *J. Membrane Sci.,* 2001, 185, 41; and Heitner-Wirguin, *J. Membrane Sci.,* 1996, 120, 1.

The compositions of this invention may be formed by mixing a functionalized fullerene molecule and/or a functionalized curved carbon nanostructure with a Group VIII metal and/or a polymer by any mixing means as typically used in the art such as a drum tumbler, double cone blender, ribbon blender, sigma blade mixer, Banbury mixer, kneader or extruder. Films may be made from the compositions of this invention by any film forming method as typically used in the art such as solvent casting on a heated surface, or thermal pressing of an extrudate.

The functionalized fullerene molecules, the functionalized curved carbon nanostructures, and the compositions of this invention, and films made therefrom, may be used in a variety of applications such as a fuel cell, battery, electrode, catalyst or sensor.

The advantageous effects of this invention are demonstrated by a series of examples, as described below. The embodiments of the invention on which the examples are based are illustrative only, and do not limit the scope of the invention.

[2+2] Cycloaddition to Fullerenes

EXAMPLE 1

Cycloaddition of $C_{60}$ with perfluoro(3-oxo-penta-4-ene)sulfonyl fluoride

Into a 70 cc stainless steel reactor is charged $C_{60}$ (50 mg, purchased from CNI), 20 mL of 1,2,4-trichlorobenzene and 3 g of perfluoro(3-oxo-penta-4-ene)sulfonyl fluoride. The reactor is cooled to −50° C., then evacuated and filled with nitrogen. The reactor is heated to 200° C. for 18 hours. The solvent is removed under vacuum to leave a brown solid. MALDI mass spec shows masses at 720, and multiple products with masses that are multiples of 282 (mass of monomer) added to 720. The solution 19F NMR spectrum confirms that the bonding of the vinyl ether molecules with $C_{60}$ is of the 2+2 functionalized type. Solid State 19F gives: −105, −109 ppm ($J_{AB}$=208 Hz; CNT-$CF_2$—); −118.8 ppm (CNT-$CF_2$—CF—); −76.5, −83.7 ppm ($J_{AB}$=150 Hz; —O—$CF_2$—); −111.6 ppm (—$CF_2$—$SO_2$F); and +45.5 ppm ($SO_2$F).

EXAMPLE 2

Hydrolysis of $C_{60}$-sulfonyl fluoride

Sulfonyl fluoride functionalized $C_{60}$ from Example 1 (20-30 mg) is suspended in 10 mL 20% KOH solution in 5/4/1 $H_2O$/MeOH/DMSO, and heated at 80° C. for 3 hrs. The homogeneous solution is neutralized to pH 7 with 10% nitric acid. The neutralized mixture is passed through a cation exchange resin column (Bio-rad: AG 50W X8 Resin, 100-200 mesh CAS [69011-20-7], approximately 20 g, 1.5 cm×22 cm) that has been washed with methanol and water. The eluted material is lyophilized to yield 24.8 mg of brown solid.

[2+2] Cycloddition to CNT

General Procedure

The CNT material is charged into a 70 mL stainless steel reactor, followed by the specified amount of solvent, followed by a perfluoroolefin. The reactor is cooled to −50° C., then evacuated and filled with nitrogen. The reactor is heated to 200° C. for the specified period of time. The product is collected by filtration over 0.2 um PTFE membrane. The solid is washed with solvents that include Vertrel® XF hydrofluorocarbon solvent from DuPont, hexane, acetone, methylene chloride and dimethylformamide ("DMF"). The resulting solid is dried under vacuum.

EXAMPLE 3

Into a 10 cc stainless steel reactor are charged 24.0 mg purified HiPco SWNTs [purchased from Carbon Nanotubes Inc., Houston, Tex. ("CNI"), dried at 250° C. for 16 hrs under high vacuum] and 0.500 mL of $CF_2$=$CFOCF_2CF(CF_3)$$OCF_2CF_2SO_2F$ ("PSEPVE") in a nitrogen dry box. The vessel is closed under nitrogen and heated with shaking at 200° C. for 24 hrs. After reaction, the vessel is attached to a vacuum line, and the contents are pumped under high vacuum at room temperature for 4 hrs. The contents are then transferred to a glass ampule equipped with a vacuum line adapter, and are then heated at 100° C. for 2 hrs and then at 200° C. for 2 hrs under high vacuum. 35.0 mg of product is recovered. TGA under high-purity $N_2$ shows a weight loss of 46% starting at about 200° C. (see Chart A in FIG. 1).

The reaction is repeated with identical quantities of reactants at 215° C. The reactor is attached to a vacuum line, chilled in dry ice, and evacuated under high vacuum. The vessel is closed under vacuum and shaken for 24 hrs at 215° C. After reaction, the vessel is attached to a vacuum line, and the volatile products are collected in a cold trap. NMR analysis shows mostly the presence of rearranged PSEPVE. After drying at 175° C. for 2 hrs under vacuum, 32.5 mg of material are recovered. TGA under high-purity $N_2$ shows a weight loss of 49% (see Chart B in FIG. 1).

EXAMPLE 4

[2+2] Cycloaddition of SWNT with Perfluoro(3-oxo-penta-4-ene)sulfonyl fluoride Into a 70 cc stainless steel reactor is charged purified HiPCo SWNT (50 mg, purchased from CNI), 20 mL of 1,2,4-trichlorobenzene and 3 g of perfluoro(3-oxo-penta-4-ene)sulfonyl fluoride. The reactor is cooled to −50° C., and then evacuated and filled with nitrogen. The reactor is heated to 200° C. for 18 hours. The reaction mixture is filtered over a 0.2 um PTFE membrane, and washed with Vertrel® XF hydrofluorocarbon solvent from DuPont (4 times), hexane, acetone, methylene chloride and DMF. The solid is dried at 110° C. in a vacuum oven to yield 70 mg of black solid. TGA/IR shows weight loss of 46%, maximizing around 300-400° C. Raman spectra of the sample shows the characteristic peaks for CNT at 2541, 1834, 1752, 1588 (tangential mode), 1549, 1274 (disorder mode), and 263 (radial mode). Solid State F19 NMR shows bands centered around −80 ppm ($OCF_3$), −110 ppm (—$OCF_2CF_2$—), and 47 ppm ($SO_2F$).

EXAMPLE 5

[2+2] Cycloaddition of SWNT with Perfluoro(3-oxo-penta-4-ene)sulfonyl fluoride Into a 70 cc stainless steel reactor is charged purified HiPCo SWNT (20 mg, purchased from CNI) and 3 g of perfluoro(3-oxo-penta-4-ene)sulfonyl fluoride. The reactor is cooled to −50° C., then evacuated and filled with nitrogen. The reactor is heated to 200° C. for 18 hours. The reaction mixture is filtered over a 0.2 um PTFE membrane, and is then washed with Vertrel® XF hydrofluorocarbon solvent from DuPont (4 times), hexane, acetone, methylene chloride and DMF. The solid is dried at 110° C. in a vacuum oven to yield a solid. TGA shows a weight loss of 41%, maximizing around 312° C.

EXAMPLE 6

[2+2] Cycloaddition of SWNT with Perfluoro(3-oxo-penta-4-ene)sulfonyl fluoride Into a stainless steel reactor is charged purified HiPCo SWNT (200 mg, purchased from CNI), 50 mL of 1,2,4-trichlorobenzene and 13 g of perfluoro(3-oxo-penta-4-ene)sulfonyl fluoride. The reactor is cooled to −50° C., then evacuated and filled with nitrogen. The reactor is heated to 200° C. for 18 hours. The reaction mixture is filtered over a 0.2 um PTFE membrane, and is washed with Vertrel® XF hydrofluorocarbon solvent from DuPont (4 times), methylene chloride, DMF (4 times), and acetone. The solid is dried at 110° C. in a vacuum oven, to yield 70 mg of a black solid. TGA shows a weight loss of 12% at greater than 200° C.

EXAMPLE 7

[2+2] Cycloaddition of SWNT with Perfluoro(3-oxo-penta-4-ene)sulfonyl fluoride Into a 70 cc stainless steel reactor is charged purified HiPCo SWNT (100 mg, purchased from CNI), 5 mL of 1,2,4-trichlorobenzene and 6 g of perfluoro(3-oxo-penta-4-ene)sulfonyl fluoride. The reactor is cooled to −50° C., then evacuated and filled with nitrogen. The reactor is heated to 200° C. for 18 hours. The reaction mixture is filtered over a 0.2 um PTFE membrane, and is washed with Vertrel® XF hydrofluorocarbon solvent from DuPont (4 times), methylene chloride, DMF (4 times), and acetone. The solid is dried at 100° C. in a vacuum oven for 2 days, then at 200° C. under vacuum for 4 hours, to yield 0.10 g of a black solid. TGA shows a weight loss of 16% at greater than 200° C.

EXAMPLE 8

[2+2] Cycloaddition of SWNT with PSEPVE

Into a 70 cc stainless steel reactor is charged purified HiPCo SWNT (50 mg, purchased from CNI), and 2.4 g of PSEPVE (perfluoro(4-methyl-3,6-dioxaoct-7-ene)sulfonyl fluoride, $CF_2$=$CFOCF_2CF(CF_3)OCF_2CF_2SO_2F$). The reactor is cooled to −50° C., then evacuated and filled with nitrogen. The reactor is heated to 200° C. for 10 hours. The reaction mixture is filtered over a 0.2 um PTFE membrane, and is washed with Vertrel® XF hydrofluorocarbon solvent from DuPont (4 times), methylene chloride, DMF (4 times), and acetone. The solid is dried at 200° C. under vacuum for 4 hours, to yield 0.10 g of a black solid. TGA showed a weight loss of 18% centered at 320° C.

EXAMPLE 9

Reaction of MWNT with $CF_2$=$CFOCF_2CF_2SO_2F$

A suspension of 0.15 g of MWNT (provided by Tsing Hua University, China), 9.0 g of $CF_2$=$CFOCF_2CF_2SO_2F$ in 20 mL of trichlorobenzene is heated in a autoclave under $N_2$ at 200° C. for 20 hrs. The reaction mixture is filtered and washed with $CH_3CN$, MeOH and $CF_2ClCFCl_2$ for 3 times and dried at 120° C. in a vacuum oven overnight. 0.157 g of black solids are obtained. TGA indicates an 8.3% weight loss when heated to 400° C.

General Procedure for the Hydrolysis of CNT-sulfonyl fluoride

Sulfonyl fluoride functionalized CNT (0.2 g) is suspended in 30 mL 20% KOH solution in 5/4/1$H_2O$/MeOH/DMSO, and heated at 80° C. for 3 hrs. The hetereogeneous solution is filtered. The solid is washed 4 times with deionized distilled water. The solid is then re-suspended in 10% $HNO_3$, and heated at 60° C. for 3 hrs. The resulting solid is then filtered, and washed with deionized distilled water until the filtrate is neutral in pH. The washed solid is then dried in a vacuum oven at 80-110° C. for 2 days, then pumped under vacuum for three days. Yield is 0.17 g. IR (KBr pellet) cm-1 shows: 3434 (medium, broad, —$SO_3H$), 1752 (weak), 1520-1570 (weak-medium), 1162 [strong, —$(CF_2)_n$].

EXAMPLE 10

Hydrolysis of CNT-Sulfonyl Fluoride

Sulfonyl fluoride functionalized CNT (0.2 g), prepared as described in Example 6, is suspended in 30 mL 20% KOH solution in 5/4/1$H_2O$/MeOH/DMSO. The mixture is sonicated for 20 minutes, then heated at 80° C. for 3 hrs. The hetereogeneous solution is filtered. The filtrate is slightly amber in color. The solid is washed 4 times with deionized distilled water ("dd water"). The solid is then re-suspended in 30 mL 10% $HNO_3$, sonicated for 20 min., and heated at 60° C. for 3 hrs. The resulting solid is then filtered, and washed with deionized distilled water until the filtrate is neutral in pH. The washed solid is then dried in a vacuum oven at 100° C. for 4 days. Yield is 0.16 g.

EXAMPLE 11

Hydrolysis of CNT-Sulfonyl Fluoride

Sulfonyl fluoride adduct of CNT from Example 7 (0.094 g) is suspended in 20 mL 20% KOH solution in 5/4/1 mixture $H_2O$/MeOH/DMSO. The mixture is sonicated for 30 minutes, then heated at 80° C. for 3 hrs. The hetereogeneous solution is filtered. The filtrate is slightly amber in color. The solid is washed 4 times with dd water. The solid is then re-suspended in 20 mL 10% $HNO_3$, sonicated for 20 min., and heated at 60° C. for 3 hrs. The resulting solid is then filtered, and washed with dd water until the filtrate is neutral in pH. The washed solid is then dried at 200° C. under vacuum, and further dried in a vacuum oven at 100° C. for 1 day. Yield is 0.076 g. TGA shows 13% weight loss at greater than 200° C. (centered around 366° C.).

Radical Addition to CNT's

EXAMPLE 12

SWNT Reaction with HFPO-Dimer Peroxide

Purified HiPCo SWNT [0.13 g (10.8 mmol) from CNI] is weighed into a 250 mL round bottom flask. The flask is filled with nitrogen. To this is added 35 mL 0.16 M (5.6 mmol) HFPO dimer peroxide solution [bis(perfluoro-2-propoxypropanoyl) peroxide] in Vertrel® XF hydrofluorocarbon solvent from DuPont. The reaction is stirred at room temperature for 12 hours under nitrogen. To this is added another 35 mL of 0.16 M HFPO dimer peroxide, and the reaction is stirred for another 7 hours, at which time another 17 mL of 0.16 M HFPO dimer peroxide solution is added. The total amount of HFPO dimer peroxide added is 87 mL of 0.16 M solution (13.9 mmol). The solid is collected by filtration, and washed with Vertrel® XF hydrofluorocarbon solvent from DuPont, hexane, acetone, methylene chloride and DMF (yellow in color), and dried under vacuum. Yield of the solid is 0.14 g. TGA of the solid shows two humps: 7% wt. loss around 200° C., and 12% around 200° C. Raman: 2541, 1834, 1752, 1588 (tangential mode of the nanotube), 1549, 1274 (disorder band, due to SP3 carbon), 326, 305, and 263 $cm^{-1}$.

EXAMPLE 13

SWNT Reaction with HFPO-Dimer Peroxide

Purified HiPCo SWNT [24 mg (2.1 mmol) from CNI] are suspended in approximately 2-5 mL Vertrel® XF hydrofluorocarbon solvent from DuPont, and sonicated for 20 min. The suspension is transferred into a 20 mL round bottom tube, and cooled on dry ice. To this is added 6 mL of 0.16 M HFPO dimer peroxide (0.96 mmol). The mixture is stirred at room temperature overnight. The solid is filtered over a 0.2 uM PTFE membrane, and washed with DMF, dimethyl sulfoxide ("DMSO"), and acetone. The solid is then suspended in chloroform, and washed with 15% HCl. The solid is collected over a 0.45 uM PTFE membrane, and dried under vacuum. TGA shows: 13% wt loss (broad hump around 300° C., and a sharp transition centered around 420° C.).

This example is repeated with raw HiPCo SWNT [36 mg (3 mmol) from CNI] and 9 mL of 0.16 M HFPO dimer peroxide (1.44 mmol) to yield 24 mg of a black solid. TGA shows: 6.5% wt loss [broad shoulder around a sharp transition (5.3%) centered around 420° C., and sharp transition (1.2%) around 500° C.].

EXAMPLE 14

SWNT Reaction with Perfluorooctyl Iodide

A suspension of purified HiPCo SWNT [10 mg (0.83 mmol) from CNI] in 30 mL perfluorotetradecahydro phenanthrene (bp. 210° C.) is sonicated at room temperature for 20 min. The suspension is charged into, a heavy-walled glass reactor, followed by perfluorooctyl iodide (MW 545.97, 0.66 g, 1.2 mmol), is de-oxygenated by freeze-pump-thaw (three cycles), and is then sealed under nitrogen. The vessel is heated at 200° C. for 7 hours. The reaction content is cooled, and the resulting suspension is filtered over a 0.2 um PTFE membrane. The solid is washed with Vertrel® XF hydrofluorocarbon solvent from DuPont, hexane, methylene chloride, DMF and acetone. The solid isolated weighs 7.6 mg. TGA shows: 21% wt loss (two broad humps: 16% centered around 320° C., and 5% around 570° C.)

EXAMPLE 15

SWNT Reaction with Perfluorooctyl Iodide

A suspension of purified HiPCo SWNT [10 mg (0.83 mmol) from CNI] in 30 mL perfluorotetradecahydro phenanthrene (bp. 210° C.) is sonicated at room temperature for 10 min. The suspension is charged into a heavy-walled glass reactor, followed by perfluorooctyl iodide (MW 545.97, 0.66 g, 1.2 mmol), is de-oxygenated by freeze-pump-thaw (three cycles), and is then sealed under nitrogen. The vessel is heated at 200° C. for 7 hours. The reaction vessel is cooled to room temperature, and another 0.66 g of perfluorooctyl iodide is added. The reaction mixture is heated for another 7 hours at 200° C. This process of adding more perfluorooctyl iodide, followed by heating at 200° C. for 7 hours is repeated 3 times. The total amount of perfluorooctyl iodide reagent used is 5×0.66 g (6 mmol). The reaction content is cooled, and the resulting suspension is filtered over a 0.2 um PTFE membrane. The solid is washed with Vertrel® XF hydrofluorocarbon solvent from DuPont, hexane, methylene chloride, DMF and acetone. Solid isolated: 7.1 mg. TGA shows: 30% wt loss (two broad humps: 17% centered around 300° C., and 13% centered around 500° C.)

EXAMPLE 16

Solventless SWNT Reaction with Perfluorohexyl Iodide

Into a 10 cc stainless steel reactor are charged 48.2 mg purified carbon nanotubes (from CNI, dried at 250° C. for 16 hr under high vacuum) and 0.85 mL 1-iodo-perfluorohexane. The reactor is chilled in dry ice for 30 min to freeze the iodide and then evacuated to high vacuum. The vessel is then closed under vacuum, and is heated at 330° C. with shaking for 4 hr. After reaction, the reactor is pumped under high vacuum for 2 hr at room temperature to remove volatile by-products. The contents of the reactor are transferred to a glass ampule equipped with a vacuum adapter. The ampule with the product is kept under high vacuum for 30 min at 320° C. to ensure complete removal of molecular iodine formed in the reaction.

64.5 mg of material is recovered (i.e. 34% gain in mass). TGA under high-purity $N_2$ showed a 27% weight loss starting at approximately 300° C.

EXAMPLE 17

SWNT Reaction with Perfluorohexyl Iodide

A suspension of raw HiPCo SWNT [6 mg (0.50 mmol) from CNI] in 10 mL perfluorotetradecahydro phenanthrene (bp. 210° C.) is sonicated at room temperature for 10 min. The suspension is charged into a heavy-walled glass reactor, followed by perfluorohexyl iodide (MW 446, 1.25 g, 2.8 mmol), is de-oxygenated by freeze-pump-thaw (three cycles), and is then sealed under nitrogen. The vessel is heated at 200° C. for 7 hours. The reaction vessel is cooled to room temperature, and another 1.25 g of perfluorooctyl iodide is added. The reaction mixture is heated for another 7 hours at 200° C. This process of adding more perfluorooctyl iodide, followed by heating at 200° C. for 7 hours is repeated 2 more times. The total amount of perfluorooctyl iodide reagent used is 1.25 g (7 h), 1.25 g (7 h), 1.6 g (18 h), 1.4 g (9 h), or a total of 5.5 g of perfluorohexyl iodide (12.3 mmol). The reaction content is cooled, and the resulting suspension is filtered over a 0.2 um PTFE membrane. The solid is washed with Vertrel® XF hydrofluorocarbon solvent from DuPont, hexane, methylene chloride, DMF and acetone. Solid isolated: 10 mg. TGA shows: 32% weight loss (three broad humps from 180-400° C.).

EXAMPLE 18

Surface Modification of Vulcan XC 72R Carbon Black by Reaction with perfluoro(3-oxo-penta-4-ene)sulfonyl fluoride Into a quartz vial (10 mm OD, ~6 cm height, with a 5 mm OD extension to facilitate attachment to a vacuum system and sealing off with a torch) are charged 11.6 mg of Vulcan XC 72R carbon (Cabot Corporation, dried under high vacuum at 250° C. for 25 hrs) and 100 μL of perfluoro(3-oxo-penta-4-ene)sulfonyl fluoride in a nitrogen glove box. The vial is attached to a vacuum manifold via an O-ring adaptor without exposing the contents to the air. The vial is immersed in liquid nitrogen, evacuated, and sealed at the neck with a torch. It is kept in a cylindrical tube furnace at 200° C. for 66 hrs. At the end of this time, the vial is opened at the neck and once again attached to the vacuum manifold for drying under vacuum for 1 hr at 175° C. TGA using high purity nitrogen (10° C./min) indicates 17% weight loss commencing above 200° C. A similar TGA of the untreated XC 72R carbon black shows no appreciable weight change up to 800° C. A repeat of the experiment with 9.8 mg of dried Vulcan carbon black and 30 μL of perfluoro(3-oxo-penta-4-ene)sulfonyl fluoride reacted at 200° C. for 64 hrs results in a TGA weight loss of 12%. The lower percentage weight losses revealed by TGA compared to the nanotubes may be explained partly by the larger particle size of the Vulcan carbon black, the lower surface curvature compared to nanotubes, and the smaller fraction of carbon atoms available for reaction.

EXAMPLE 19

Surface Modification of TKK TEC10 Carbon Black Supporting Pt Nanoparticles by Reaction with perfluoro(3-oxo-penta-4-ene)sulfonyl fluoride Into a quartz vial (10 mm OD, —6 cm height, with a 5 mm OD extension to facilitate attachment to a vacuum system and sealing off with a torch, dried at 110° C. for 16 hr under vacuum) are charged 10.1 mg of TKK TEC10 E50E Pt-imbedded carbon black (TANAKA PRECIOUS METALS Group, dried under high vacuum at 250° C. for 20 hrs), and 39.8 mg of perfluoro(3-oxo-penta-4-ene)sulfonyl fluoride in a nitrogen glove box. The vial is attached to a vacuum manifold via an O-ring adaptor without exposing the contents to the air. The vial is immersed in liquid nitrogen, evacuated, degassed by threefold freeze-thaw pumping, and sealed at the neck with a torch. It is kept in a cylindrical tube furnace at 200° C. for 68 hrs. At the end of this time, the vial is opened at the neck and once again attached to the vacuum manifold for drying under vacuum for 1 hr at 175° C. TGA using high purity nitrogen (10° C./min) indicates 28% weight loss commencing above 200° C. A similar TGA of the untreated TKK carbon black shows less than 7% weight loss up to 600° C.

Formation of Compositions and Films

EXAMPLE 20

A small vial is charged with 5 mg of functionalized SWNTs from Example 10, 102 mg of freeze-dried Nafion® 1100 fluorinated polymer from DuPont and 2 mL of n-BuOH. The resulting mixture is stirred at room temperature for 40 hrs, and a black dispersion is obtained. The dispersion is poured onto a glass plate in a hood. After most of the n-BuOH has evaporated, the glass plate is heated at 165-170° C. in a vacuum oven for 1.5 hrs. The black film is peeled off and treated with 10% $HNO_3$ at room temperature overnight, and washed with de-ionized water to neutral to give a 1 mil thick film. Conductivity in plane is 783 mS/cm at 120° C. under 25% relative humidity.

EXAMPLE 21

A small vial is charged with 12 mg of functionalized SWNTs from Example 12, 100 mg of freeze dried Nafion® 1100 fluorinated polymer from DuPont and 2 mL of n-butanol and 6 mL of water. The resulting mixture is stirred at room temperature for 72 hours, and a black dispersion is obtained. The dispersion is poured onto a glass plate in a hood. After most of the n-BuOH has evaporated, the glass plate is heated at 130-190° C. in a vacuum oven for 1 hr. The black film is peeled off and treated with 10% $HNO_3$ at room temperature overnight, and washed with de-ionized water to neutral to give a 1 mil thick film. Conductivity in plane is 18327 mS/cm at room temperature under 95% relative humidity.

EXAMPLE 22

In an approximately 20 mL scintillation vial, 18 mg of Pt/Ru catalyst (purchased from Johnson Mathey, HiSPEC 6020), 2 mg of the functionalized SWNTs from Example 10 and 1 mL of a 4.8 wt % solution of Nafion® 1100 fluorinated polymer from DuPont (2:1:1 water, 1-propanol, 2-propanol) are combined and sonicated in a sonication bath for 30 minutes, to form a catalyst ink. 25 μL of that solution is loaded onto a 1 $cm^2$ area of 1 cm×5 cm carbon paper electrode strip and allowed to dry in the hood overnight. The activity of the dried ink mixture towards methanol oxidation is measured in a standard half-cell electrochemical experiment in a 0.5M $H_2SO_4$ and 1M $CH_3OH$ solution. The polarization curves [current (I) vs. potential (V)] indicate that the mixture does oxidize methanol with an onset potential of approximately 0.2V vs. a saturated calomel reference electrode.

Where a material or composition of this invention is stated or described as comprising, including, containing, having, being composed of or being constituted by certain components, it is to be understood, unless the statement or description explicitly provides to the contrary, that one or more components in addition to those explicitly stated or described may be present in the material or composition. In an alternative embodiment, however, a material or composition of this invention may be stated or described as consisting essentially of certain components, in which embodiment components that would materially alter the principle of operation or the distinguishing characteristics of the materials or composition are not present therein. In a further alternative embodiment, a material or composition of this invention may be stated or described as consisting of certain components, in which embodiment components other than impurities are not present therein.

Where the indefinite article "a" or "an" is used with respect to a statement or description of the presence of a component in a material or composition of this invention, it is to be understood, unless the statement or description explicitly provides to the contrary, that the use of such indefinite article does not limit the presence of the component in the material or composition to one in number.

What is claimed is:

1. A fullerene molecule comprising n carbon atoms wherein m groups described generally by the formula

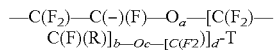

are each covalently bonded to the fullerene through formation of a 4-member ring with the unsaturated pi system of the fullerene; and wherein
 a is 0 or 1;
 b is 0 to 10;
 c is 0 or 1;
 d is 1 to 10;
 each R is independently selected from the group consisting of H, F, methyl, branched or straight-chain perfluorinated $C_1$-$C_{10}$ alkyl, phenyl and perfluorinated aryl groups;
 each T is independently selected from the group consisting of —$CO_2H$, —$SO_3H$, —$SO_2NH_2$, —$SO_2NHSO_2J$ and —$PO_3H_2$ groups;
 each J is independently selected from the group consisting of F, methyl, branched or straight-chain perfluorinated $C_1$-$C_{10}$ alkyl, phenyl and perfluorinated aryl groups;
 n is an integer from 20 to 1000; and
 m is an integer from 1 to n/2 when n is an even integer, or is an integer from 1 to (n−1)/2 when n is an odd integer.

2. A fullerene molecule according to claim 1 wherein T is selected from the group consisting of —$SO_3H$, —$SO_2NH_2$, —$SO_2NHSO_2J$ and —$PO_3H_2$ groups, and J is F or $CF_3$ groups.

3. A fullerene molecule according to claim 1 wherein n is 60 to 100.

4. A fullerene molecule comprising n carbon atoms wherein m groups described generally by the formula

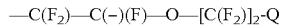

are each covalently bonded to the fullerene through formation of a 4-member ring with the unsaturated pi system of the fullerene; and wherein
 each Q is independently selected from the group consisting of —COG, —CN, —$SO_2F$ groups;
 each G is independently selected from F, Cl, $C_1$-$C_8$ alkoxy and $C_6$-$C_{12}$ aryloxy groups;

n is an integer from 20 to 1000; and
 m is an integer from 1 to n/2 when n is an even integer, or is an integer from 1 to (n−1)/2 when n is an odd integer.

5. A fullerene molecule according to claim 4 wherein Q is —$SO_2F$.

6. A fullerene molecule according to claim 4 wherein n is 60 to 100.

7. A fullerene molecule comprising n carbon atoms wherein m groups described generally by the formula

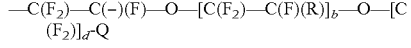

are each covalently bonded to the fullerene through formation of a 4-member ring with the unsaturated pi system of the fullerene; and wherein
 b is 1 to 10;
 d is 1 to 10;
 each R is independently selected from the group consisting of H, F, methyl, branched or straight-chain perfluorinated $C_1$-$C_{10}$ alkyl, phenyl and perfluorinated aryl groups;
 each Q is independently selected from the group consisting of —COG, —CN, —$SO_2F$ groups;
 each G is independently selected from F, Cl, $C_1$-$C_8$ alkoxy and $C_6$-$C_{12}$ aryloxy groups;
 n is an integer from 20 to 1000; and
 m is an integer from 1 to n/2 when n is an even integer, or is an integer from 1 to (n−1)/2 when n is an odd integer.

8. A fullerene molecule according to claim 7 wherein Q is —$SO_2F$.

9. A fullerene molecule according to claim 7 wherein n is 60 to 100.

10. A fullerene molecule comprising n carbon atoms wherein m groups described generally by the formula

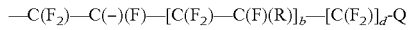

are each covalently bonded to the fullerene through formation of a 4-member ring with the unsaturated pi system of the fullerene; and wherein
 b is 0 to 10;
 d is 1 to 10;
 each R is independently selected from the group consisting of H, F, methyl, branched or straight-chain perfluorinated $C_1$-$C_{10}$ alkyl, phenyl and perfluorinated aryl groups;
 each Q is independently selected from the group consisting of —COG, —CN, —$SO_2F$ groups;
 each G is independently selected from F, Cl, $C_1$-$C_8$ alkoxy and $C_6$-$C_{12}$ aryloxy groups;
 n is an integer from 20 to 1000; and
 m is an integer from 1 to n/2 when n is an even integer, or is an integer from 1 to (n−1)/2 when n is an odd integer.

11. A fullerene molecule according to claim 10 wherein Q is —$SO_2F$.

12. A fullerene molecule according to claim 10 wherein n is 60 to 100.

13. A curved carbon nanostructure comprising carbon atoms wherein m groups described generally by the formula

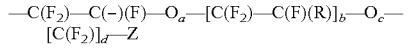

are each covalently bonded to the nanostructure through formation of a 4-member ring with an unsaturated pi system of the nanostructure; and wherein
 a is 0 or 1;
 b is 0 to 10;
 c is 0 or 1;
 d is 1 to 10;

each R is independently selected from the group consisting of H, F, methyl, branched or straight-chain perfluorinated $C_1$-$C_{10}$ alkyl, phenyl and perfluorinated aryl groups;

each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;

each G is independently selected from F, Cl, $C_1$-$C_8$ alkoxy and $C_6$-$C_{12}$ aryloxy groups;

each J is independently selected from the group consisting of F, methyl, branched or straight-chain perfluorinated $C_1$-$C_{10}$ alkyl, phenyl and perfluorinated aryl groups; and m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer.

14. A curved carbon nanostructure according to claim 13 wherein Z is selected from the group consisting of —$SO_3H$, —$SO_2NH_2$, —$SO_2NHSO_2J$ and —$PO_3H_2$ groups, and J is F or $CF_3$ groups.

15. A curved carbon nanostructure according to claim 13 wherein the curved carbon nanostructure is a carbon nanotube.

16. A curved carbon nanostructure according to claim 15 wherein the carbon nanotube is electrically conductive.

17. A curved carbon nanostructure according to claim 13 wherein the curved carbon nanostructure is carbon black.

18. A fullerene molecule comprising n carbon atoms wherein m groups described generally by the formula

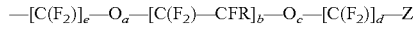

are each covalently bonded to an individual carbon atom of the fullerene; and wherein a is 0 or 1;
b is 0 to 10;
c is 0 or 1;
d is 1 to 10;
e is 0 to 10;

each R is independently selected from the group consisting of H, F, methyl, branched or straight-chain perfluorinated $C_1$-$C_{10}$ alkyl, phenyl and perfluorinated aryl groups;

each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;

each G is independently selected from F and Cl;

each J is independently selected from the group consisting of F, methyl, branched or straight-chain perfluorinated $C_1$-$C_{10}$ alkyl, phenyl and perfluorinated aryl groups;

n is an integer from 20 to 1000;

m is an integer from 1 to n/2 when n is an even integer, or is an integer from 1 to (n−1)/2 when n is an odd integer; and p groups selected from hydrogen and halogen are each covalently bonded to an individual carbon atom of the fullerene where p is an integer from 0 to m.

19. A fullerene molecule according to claim 18 wherein Z is selected from the group consisting of —$SO_3H$, —$SO_2NH_2$, —$SO_2NHSO_2J$ and —$PO_3H_2$ groups, and J is F or $CF_3$ groups.

20. A fullerene molecule according to claim 18 wherein n is 60 to 100.

21. A curved carbon nanostructure comprising carbon atoms wherein m groups described generally by the formula

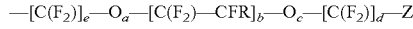

are each covalently bonded to an individual carbon atom in the nanostructure; and wherein a is 0 or 1;
b is 0 to 10;
c is 0 or 1;
d is 1 to 10;
e is 0 to 10;

each R is independently selected from the group consisting of H, F, methyl, branched or straight-chain perfluorinated $C_1$-$C_{10}$ alkyl, phenyl and perfluorinated aryl groups;

each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;

each G is independently selected from F and Cl;

each J is independently selected from the group consisting of F, methyl, branched or straight-chain perfluorinated $C_1$-$C_{10}$ alkyl, phenyl and perfluorinated aryl groups;

m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer; and p groups selected from hydrogen and halogen are each covalently bonded to an individual carbon atom of the nanostructure where p is an integer from 0 to m.

22. A curved carbon nanostructure according to claim 21 wherein Z is selected from the group consisting of —$SO_3H$, —$SO_2NH_2$, —$SO_2NHSO_2J$ and —$PO_3H_2$ groups, and J is F or $CF_3$ groups.

23. A curved carbon nanostructure according to claim 21 wherein the curved carbon nanostructure is a carbon nanotube.

24. A curved carbon nanostructure according to claim 23 wherein the carbon nanotube is electrically conductive.

25. A curved carbon nanostructure according to claim 21 wherein the curved carbon nanostructure is carbon black.

26. A composition of matter comprising a fullerene molecule according to any one of claim 1, 4, 7, 10 or 18, and a curved carbon nanostructure that comprises carbon atoms wherein m groups described generally by the formula

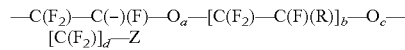

are each covalently bonded to the nanostructure through formation of a 4-member ring with an unsaturated pi system of the nanostructure; and wherein a is 0 or 1;
b is 0 to 10;
c is 0 or 1;
d is 1 to 10;

each R is independently selected from the group consisting of H, F, mehtyl, branched or straight-chain perfluorinated $C_1$-$C_{10}$ alkyl, phenyl and perfluorinated aryl groups;

each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;

each G is independently selected from F, Cl, $C_1$-$C_8$ alkoxy and $C_6$-$C_{12}$ aryloxy groups;

each J is independently selected from the group consisting of F, methyl, branched or straight-chain perfluorinated $C_1$-$C_{10}$ alkyl, phenyl and perfluorinated aryl groups; and m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer.

27. A composition of matter comprising a fullerene molecule according to any one of claim 1, 4, 7, 10 or 18, and a polymer.

28. A composition of matter comprising a fullerene molecule according to any one of claim 1, 4, 7, 10 or 18, and a Group VIII metal.

29. A composition according to claim 27 further comprising a Group VIII metal.

30. A composition of matter comprising a curved carbon nanostructure according to claim 13 or 21 and a polymer.

31. A composition of matter comprising a curved carbon nanostructure according to claim 13 or 21 and a Group VIII metal.

32. A composition according to claim 30 further comprising a Group VIII metal.

33. A composition of matter comprising a fullerene molecule according to any one of claim 1, 4, 7, 10 or 18, a curved carbon nanostructure, and a polymer;
wherein the curved carbon nanostructure comprises carbon atoms wherein m groups described generally by the formula

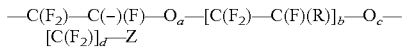

are each covalently bonded to the nanostructure through formation of a 4-member ring with an unsaturated pi system of the nanostructure; and wherein
a is 0 or 1;
b is 0 to 10;
c is 0 or 1;
d is 1 to 10;
each R is independently selected from the group consisting of H, F, methyl, branched or straight-chain perfluorinated $C_1$-$C_{10}$ alkyl, phenyl and perfluorinated aryl groups;
each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;
each G is independently selected from F, Cl, $C_1$-$C_8$ alkoxy and $C_6$-$C_{12}$ aryloxy groups;
each J is independently selected from the group consisting of F, methyl, branched or straight-chain perfluorinated $C_1$-$C_{10}$ alkyl, phenyl and perfluorinated aryl groups; and
m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer.

34. A composition of matter comprising a fullerene molecule according to any one of claim 1, 4, 7, 10 or 18, a curved carbon nanostructure, and a Group VIII metal;
wherein the curved carbon nanostructure comprises carbon atoms wherein m groups described generally by the formula

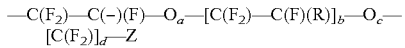

are each covalently bonded to the nanostructure through formation of a 4-member ring with an unsaturated pi system of the nanostructure; and wherein
a is 0 or 1;
b is 0 to 10;
c is 0 or 1;
d is 1 to 10;
each R is independently selected from the group consisting of H, F, methyl, branched or straight-chain perfluorinated $C_1$-$C_{10}$ alkyl, phenyl and perfluorinated aryl groups;
each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;
each G is independently selected from F, Cl, $C_1$-$C_8$ alkoxy and $C_6$-$C_{12}$ aryloxy groups;
each J is independently selected from the group consisting of F, methyl, branched or straight-chain perfluorinated $C_1$-$C_{10}$ alkyl, phenyl and perfluorinated aryl groups; and
m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer.

35. A composition according to claim 33 further comprising a Group VIII metal.

36. A composition of matter comprising a fullerene molecule according to any one of claim 1, 4, 7, 10 or 18, and a curved carbon nanostructure that comprises carbon atoms wherein m groups described generally by the formula

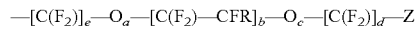

are each covalently bonded to an individual carbon atom in the nanostructure; and wherein
a is 0 or 1;
b is 0 to 10;
c is 0 or 1;
d is 1 to 10;
e is 0 to 10;
each R is independently selected from the group consisting of H, F, methyl, branched or straight-chain perfluorinated $C_1$-$C_{10}$ alkyl, phenyl and perfluorinated aryl groups;
each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;
each G is independently selected from F, Cl;
each J is independently selected from the group consisting of F, methyl, branched or straight-chain perfluorinated $C_1$-$C_{10}$ alkyl, phenyl and perfluorinated aryl groups; and
m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer; and
p group selected from hydrogen and halogen are each covalently bonded to an individual carbon atom of the nanostructure where p is an integer from 0 to m.

37. A composition of matter comprising a fullerene molecule according to any one of claim 1, 4, 7, 10 or 18, a curved carbon nanostructure, and a polymer;
wherein the curved carbon nanostructure comprises carbon atoms wherein m groups described generally by the formula

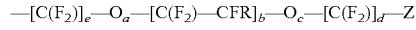

are each covalently bonded to an individual carbon atom in the nanostructure; and wherein
a is 0 or 1;
b is 0 to 10;
c is 0 or 1;
d is 1 to 10;

e is 0 to 10;

each R is independently selected from the group consisting of H, F, methyl, branched or straight-chain perfluorinated $C_1$-$C_{10}$ alkyl, phenyl and perfluorinated aryl groups;

each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;

each G is independently selected from F, Cl;

each J is independently selected from the group consisting of F, methyl, branched or straight-chain perfluorinated $C_1$-$C_{10}$ alkyl, phenyl and perfluorinated aryl groups;

m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer; and p group selected from hydrogen and halogen are each covalently bonded to an individual carbon atom of the nanostructure where p is an integer from 0 to m.

38. A composition of matter comprising a fullerene molecule according to any one of claim 1, 4, 7, 10 or 18, a curved carbon nanostructure, and a Group VIII metal;

wherein the curved carbon nanostructure comprises carbon atoms wherein m groups described generally by the formula

are each covalently bonded to an individual carbon atom in the nanostructure; and wherein a is 0 or 1;

b is 0 to 10;

c is 0 or 1;

d is 1 to 10;

e is 0 to 10;

each R is independently selected from the group consisting of H, F, methyl, branched or straight-chain perfluorinated $C_1$-$C_{10}$ alkyl, phenyl and perfluorinated aryl groups;

each Z is independently selected from the group consisting of —$CO_2H$, —COG, —CN, —$SO_2F$, —$SO_3H$, —$SO_2NH_2$, —$SO_2NHSO_2J$ and —$PO_3H_2$ groups;

each G is independently selected from F, Cl;

each J is independently selected from the group consisting of F, methyl, branched or straight-chain perfluorinated $C_1$-$C_{10}$ alkyl, phenyl and perfluorinated aryl groups; and m is an integer from 1 to half of the number of carbon atoms in the nanostructure in the case where the number of carbon atoms in the nanostructure is an even integer, or m is an integer from 1 to half minus 0.5 of the number of carbon atoms in the nanostructure when the number of carbon atoms in the nanostructure is an odd integer; and p group selected from hydrogen and halogen are each covalently bonded to an individual carbon atom of the nanostructure where p is an integer from 0 to m.

* * * * *